(12) United States Patent
Carpenter et al.

(10) Patent No.: US 10,744,011 B2
(45) Date of Patent: Aug. 18, 2020

(54) MONOLITHIC MEDICAL DEVICES AND METHODS OF USE

(71) Applicant: Vactronix Scientific, LLC, Fremont, CA (US)

(72) Inventors: Scott Carpenter, Fremont, CA (US); Michael Poor, Fremont, CA (US)

(73) Assignee: Vactronix Scientific, LLC, Fremont, CA (US)

( * ) Notice: Subject to any disclaimer, the term of this patent is extended or adjusted under 35 U.S.C. 154(b) by 189 days.

(21) Appl. No.: 15/149,788

(22) Filed: May 9, 2016

(65) Prior Publication Data

US 2017/0035589 A1 Feb. 9, 2017

Related U.S. Application Data

(63) Continuation of application No. PCT/US2014/064754, filed on Nov. 10, 2014.

(60) Provisional application No. 61/902,043, filed on Nov. 8, 2013, provisional application No. 61/905,049, filed on Nov. 15, 2013.

(51) Int. Cl.
*A61F 2/82* (2013.01)
*A61F 2/915* (2013.01)
*A61F 2/01* (2006.01)

(52) U.S. Cl.
CPC .......... *A61F 2/915* (2013.01); *A61F 2/013* (2013.01); *A61F 2002/91508* (2013.01); *A61F 2002/91516* (2013.01); *A61F 2002/91525* (2013.01); *A61F 2002/91575* (2013.01); *A61F 2002/91583* (2013.01); *A61F 2240/001* (2013.01); *A61F 2250/0018* (2013.01)

(58) Field of Classification Search
CPC ........................................................ A61F 2/82
See application file for complete search history.

(56) References Cited

U.S. PATENT DOCUMENTS

| 5,925,061 A | 7/1999 | Ogi et al. ............... 606/198 |
| 6,059,822 A | 5/2000 | Kanesaka et al. ............... 623/1 |
| 6,190,406 B1 | 2/2001 | Duerig et al. .............. 623/1.2 |
| 2006/0122685 A1 | 6/2006 | Bonsignore et al. ........ 623/1.13 |

(Continued)

FOREIGN PATENT DOCUMENTS

| EP | 1941848 | 7/2008 |
| WO | WO2007005800 | 1/2007 |
| WO | WO2009/012417 | 1/2009 |

OTHER PUBLICATIONS

European Extended Search Report and Written Opinion in corresponding foreign Application No. EP 14860958.9-1654, pp. 1-11 (dated Oct. 25, 2017).

(Continued)

*Primary Examiner* — Matthew W Schall
(74) *Attorney, Agent, or Firm* — David G. Rosenbaum; Benjamin D. Rotman; Rosenbaum IP, P.C.

(57) ABSTRACT

A monolithic device comprising an ultra-dense stent cell pattern including a plurality of structural members that diverts the majority of blood flow without restricting blood flow completely. The method of making medical devices comprises vapor depositing an initial film onto a substrate, laser cutting a device pattern through the initial film, electropolishing the patterned device while disposed on the substrate, and releasing the patterned device from the substrate.

20 Claims, 18 Drawing Sheets

(56) References Cited

U.S. PATENT DOCUMENTS

| | | |
|---|---|---|
| 2006/0173531 A1 | 8/2006 | Richter |
| 2009/0024205 A1* | 1/2009 | Hebert ...................... A61F 2/91 623/1.16 |
| 2011/0190872 A1 | 8/2011 | Anukhin et al. |
| 2011/0078344 A1 | 11/2011 | Thompson ................... 623/1.16 |
| 2012/0078344 A1 | 3/2012 | Kao ............................. 623/1.16 |
| 2012/0209366 A1 | 8/2012 | Sudo et al. .................. 623/1.11 |
| 2012/0282391 A1 | 11/2012 | Palmaz et al. ............... 427/2.25 |

OTHER PUBLICATIONS

International Search Report issued in corresponding foreign Application No. PCT/US2014/064754, pp. 1-4 (dated Jun. 4, 2015).
International Preliminary Report on Patentability issued in corresponding foreign Application No. PCT/US2014/064754, pp. 1-6 (dated May 19, 2016).
Written Opinion issued in corresponding foreign Application No. PCT/US2014/064754, pp. 1-4 (dated Jun. 4, 2015).

* cited by examiner

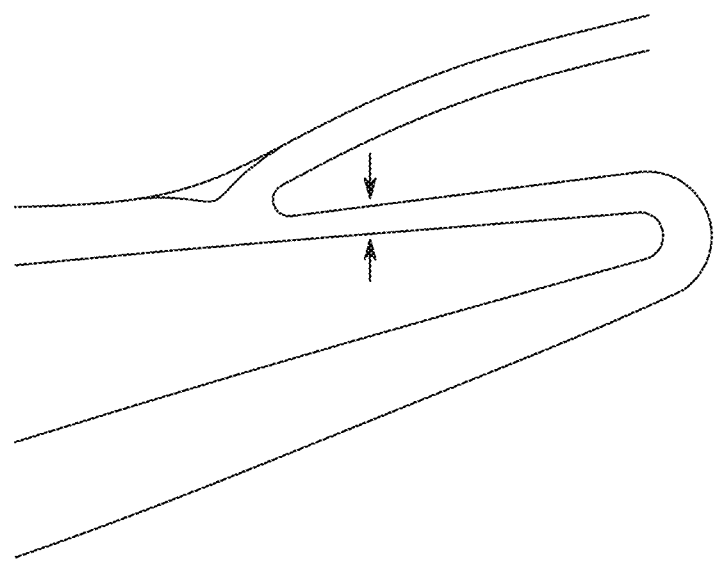
FIG. 6
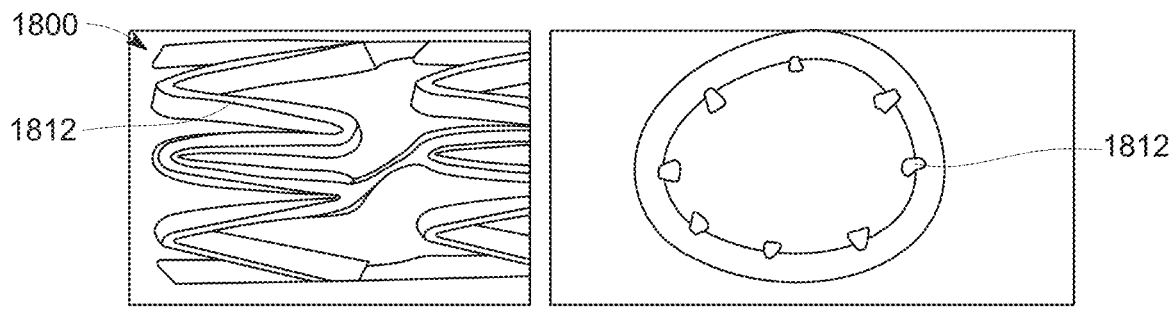
FIG. 18A
FIG. 18C
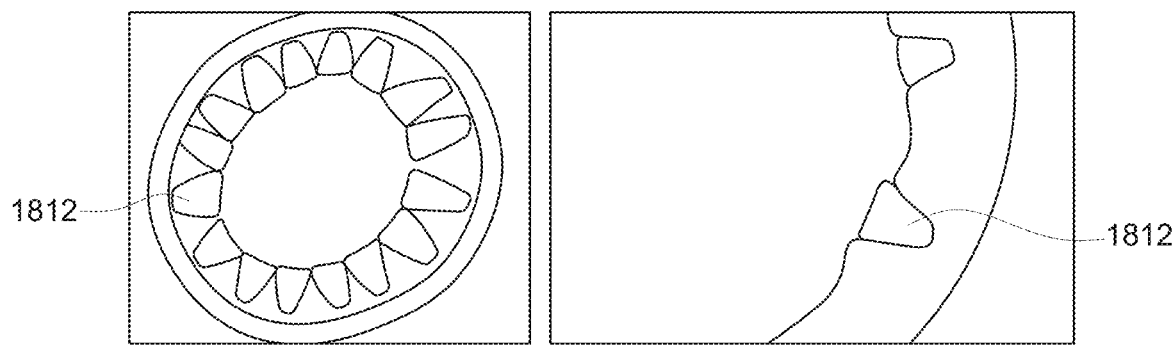
FIG. 18B
FIG. 18D

MONOLITHIC MEDICAL DEVICES AND METHODS OF USE

CROSS-REFERENCE TO RELATED APPLICATIONS

The present application claims priority to and is a continuation from PCT Application No. PCT/US2014/064754, filed Nov. 10, 2014, which claims priority from U.S. Provisional Application Ser. No. 61/902,043, filed Nov. 8, 2013 and U.S. Provisional Application Ser. No. 61/905,049, filed Nov. 15, 2013, all of which are herein incorporated by reference in their entireties.

BACKGROUND

The invention relates generally to medical devices and methods for using the same.

Various types of intravascular stents have been used in recent years. An intravascular stent generally refers to a device used for the support of living tissue during the healing phase, including the support of internal structures. Intravascular stents, or stents, placed intraluminally, as by use of a catheter device, have been demonstrated to be highly efficacious in initially restoring patency to sites of vascular occlusion. Intravascular stents, or stents, may be of the balloon-expandable type, such as those of U.S. Pat. Nos. 4,733,665; 5,102,417; or 5,195,984, which are distributed by Johnson & Johnson Interventional Systems, of Warren, N.J., as the Palmaz™ and the Palmaz-Schatz™ balloon-expandable stents or balloon expandable stents of other manufacturers, as are known in the art. Other types of intravascular stents are known as self-expanding stents, such as Nitinol coil stents or self-expanding stents made of stainless steel wire formed into a zigzag tubular configuration.

Prior art stents have some functional limitations due to their current design. For example, the prior art stent can collapse when it is bent around a sharp angle. What is needed is an improved stent that is more flexible and can be implanted in tightly bent vessels.

SUMMARY OF THE INVENTION

Provided herein are systems, methods and compositions for monolithic medical devices and methods of use.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 6 illustrates one embodiment utilizing strut tapering.

FIGS. 18A-D illustrate various views of one embodiment of a device for clot retrieval.

Figures 31, 32:
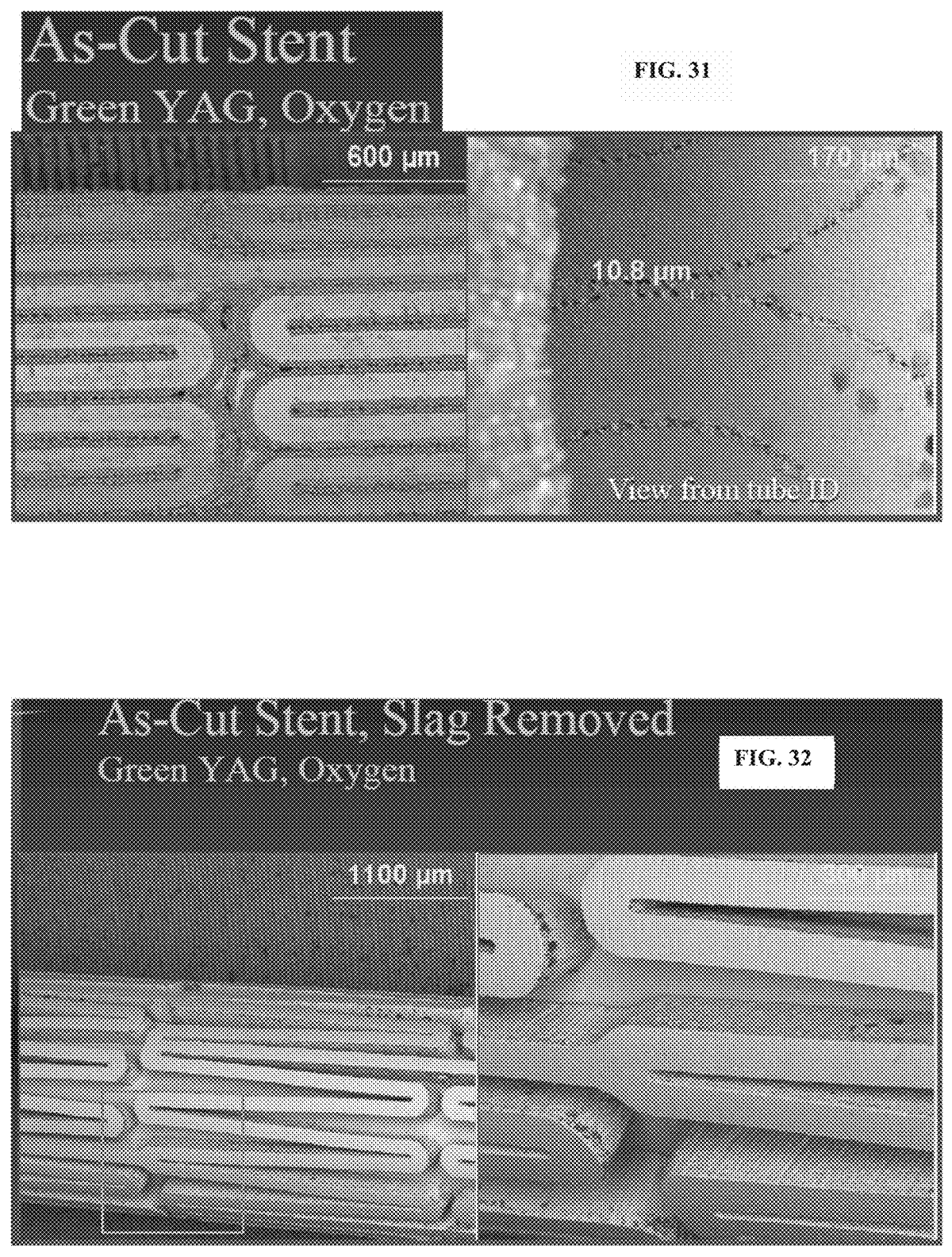

FIGS. 29-33 show SEM images of as-cut stents using standard YAG lasers with Argon cover gas, using standard YAG lasers with Oxygen assist gas, and using green YAG lasers with Oxygen assist gas.

DETAILED DESCRIPTION OF THE INVENTION

Figure 1A:
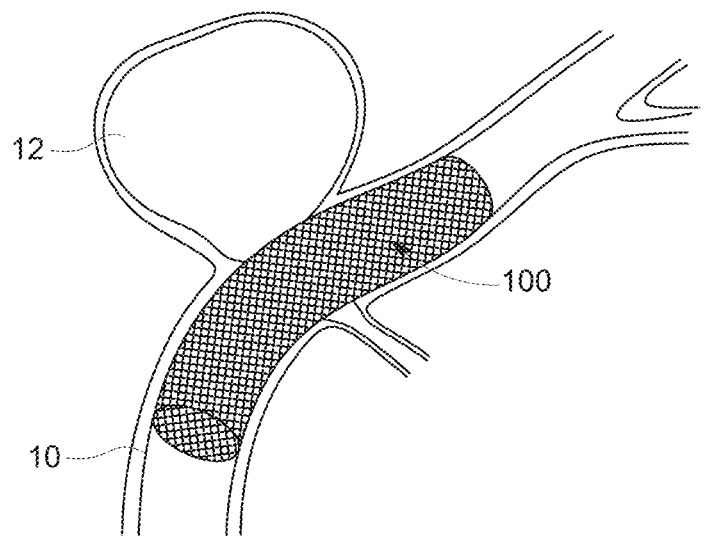
FIG. 1A is a perspective view of the monolithic device preserving flow in a blood vessel while diverting flow from an aneurysm.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Generally speaking, the monolithic devices comprise a main body structure, which provides radial force and primary structure. The main body structure is interconnected by bridges, which comprise a secondary superimposed substructure which provides flexibility, conformability, coverage, and the like. Having superimposed patterns in a single device results in a lower profile than a multicomponent device (such as a covered stent or braid). This also minimizes cost as no assembly is required. The single component also means there is no friction between components, such as in the case of covered stents or braids. Frictional effects interfere with deployment and can contribute to fretting corrosion and wear. Having a low profile minimizes flow interruption and aids in recrossability. The monolithic devices include an expanded state and a contracted state for delivery. In some embodiments, the devices utilize novel bridge configurations which add to the performance of monolithic devices.

In one embodiment, the invention comprises the use of bridges with differing stiffnesses along the device to add an additional framework, or backbone, substructure to the device. The stiffness of the bridges may be altered by increasing the width of the bridge legs. Other ways of altering the stiffness of the bridges include altering the geometries of the bridges. In addition, variations in the geometry of the bridges which control the bridge stiffness in different directions may also be advantageous. For example, it may be desirable to have bridges be relatively weak in the radial direction to aid in crimping while being stiff in the length axis to provide axial stiffness. The pattern of stiff bridges can be in various patterns to aid in kink resistance, conformability, and uniformity in bends. These patterns may be arranged in a helical or diamond array, for example.

The use of varying bridge stiffness provides an additional design feature for optimizing and controlling device performance both locally and globally. For example, bridge stiffness ratios of 4-6.5:1 show excellent kink resistance and uniform bending.

The bridges serve several functions, including: connecting the body rows; kink resistance; conformability; coverage density; maintenance of body row spacing; secondary radial force influence; crimpability; and pushability. The bridges may be designed to nest during crimping, which may aid in pushability of the device in the crimped state. Having all of the body rows fully connected with bridges at every cell increases the coverage density and makes retrievability possible. These bridges serve a dual purpose: 1) integration of the device into a single unit, and 2) adding density and coverage (useful for flow diversion, patches, closure devices, etc.). Adding nipples to the hinge points may aid in folding of the structure for crimping.

In some embodiments, the devices utilize novel structure configurations which add to the performance of monolithic devices. In some embodiments, the struts of the body rows may be altered to minimize the crimped device size by making space for the bridge features and their connection points. These adjustments may include: tapering of the struts toward their midpoint; keyholing the connection points for lower profile; or distorting the body struts to allow clearance for a bridge feature when crimped. Optimization of the crimped profile may be achieved by superstructure features such as tapering, keyholing, or local distortion of body struts to accommodate bridge features.

In some embodiments, in order to save space, a hybrid bridge connection is helpful wherein the bridge is connected on a strut tip at one end and mid-strut at the opposing end. This eliminates one leg of the bridge. The mid-strut may be a connection away from the tip or trough. In some embodiments, bridges may connect mid-strut at both ends. In some embodiments, the bridges may comprise a mid-strut outer connection. In some embodiments, the bridges may comprise a mid-strut outer opposite connection. These options may increase coverage, and allow further tuning of bridge stiffnesses. Employment of mid-strut connections reduces the impact of bridge resistive forces on kinking of the body rows, especially in bending. Mid-strut connections may also greatly reduce foreshortening, which increases device placement accuracy. High device placement accuracy allows shorter devices to be used and lowers the risk of having to place multiple devices to cover a treatment area.

In some embodiments, a coarser structure may be added to the ends of the device. This may be implemented for locally increasing radial force for anchoring, or to ease flaring. The optionally added coarse structural ends may have anchoring and/or flaring capability. These features may allow the main body to have lower radial force and may aid in bridging fusiform aneurysms.

In some embodiments, the struts may be split to increase coverage.

High density designs inherently have low alternating strains due to the strains being shared by many elements. This enhances fatigue resistance. These high density patterns spread the forces over more elements, thereby decreasing the contact stress on the vessel.

The monolithic technologies may also apply to many other uses. In general stenting, the monolithic technologies may be applied when permit tighter radial pressure control, fine features, high conformability, coverage control, lower profile, radiopacity, and/or the like are important. The monolithic technologies may be applied to integral baskets or filters, e.g., embolic protection, retrieval baskets (e.g., kidney stones), dialysis filters, and/or the like. The monolithic technologies may be applied to clot retrieval, where a wedge cross section (smaller at outer diameter than inner diameter) may aid penetration and anchoring. The monolithic technologies may be applied to patches, e.g., perforation, wound closure, spinal disc containment, and/or the like. The monolithic technologies may be applied to plaque containment (e.g., carotid, coronary, and/or the like). The monolithic technologies may be applied to flow diversion or flow obstruction. The monolithic technologies may be applied to SFA, with high axial conformability via weak/strong segments. The monolithic technologies may be applied to small vessels, i.e. ED, BTK, distal coronary, and/or the like. The monolithic technologies may be applied to scaffolding for tissue growth, i.e. heart valves, PFO (septal defects closure), and/or the like. The monolithic technologies may be applied to drainage shunts, such as urethral, bile, ocular, ear, wound, and/or the like. The monolithic technologies may be applied to grafts, such as SVG, AAA, renal, and/or the like. The monolithic technologies may be applied to drug delivery (maximize surface area and coverage), or drug eluting balloon cages. The monolithic technologies may be applied to local cancer treatment. The monolithic technologies may be applied to coronary sinus support. The monolithic technologies may be applied to tissue scaffolds. The monolithic technologies may be applied to bifurcations (compliant mesh section allowing additional stent to pass through to side branch). The monolithic technologies may be applied to cranial meshes with or without anchoring. The monolithic technologies may be applied to urinary tract stents, whether permanent or temporary, or in some instances made of resorbable materials. The monolithic technologies may be applied to contraceptive devices, such as a filter in the fallopian tube (permanent, resorbable, or removable), and/or the like. The monolithic technologies may be applied to hernia meshes, such as laparoscopy-compatible. The monolithic technologies may be applied to glaucoma shunts. The monolithic technologies may be applied to neural stimulation anchor elements. The monolithic technologies may be applied to bronchial "stents." The monolithic technologies may be applied to esophageal stents, including with drug elution. The monolithic technologies may be applied to Eustachian tube shunts. The monolithic technologies may be applied to nasal support for rhinoplasty. The monolithic technologies may be applied to delivery system linings. The monolithic technologies may be applied to anchors, such as for tissue attachment, neuro stimulation, pacing leads, vessel attachment (CABG), and/or the like. The monolithic technologies may be applied to cochlear implants. The monolithic technologies may be applied to pediatric devices, which need smaller sizes or growth accommodation, e.g., stiff axial ribs for vessel incorporation with weak bridges that allow for vessel diametric growth (may need coatings, etc. to prevent incorporation until maturity). The monolithic technologies may be applied to sensor elements, such as for coronary mapping, force feedback, and/or the like. The monolithic technologies may be applied to steerable catheters. The monolithic technologies may be applied to ablation tips. The monolithic technologies may be applied to RO position markers, whether retrievable or permanent. The monolithic technologies may be applied to MEMS devices, such as actuators, springs, valves, and/or the like. The monolithic technologies may be applied to micro-robotics components.

Figure 1B:
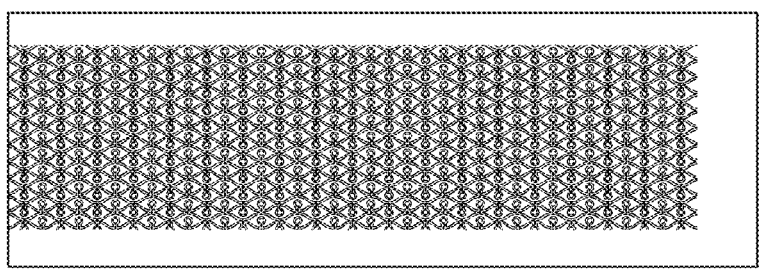
FIG. 1B illustrates one embodiment of a monolithic device, shown next to a penny for general context as to size.
Figure 1C:
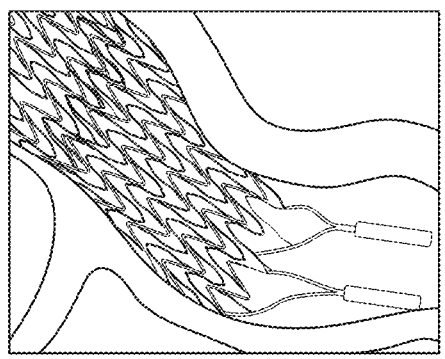
FIG. 1C shows one embodiment of the monolithic device conforming to a tortuous patient anatomy model.

Generally speaking, the monolithic device 100 is a low profile stent that promotes aneurysm 12 thrombosis by diverting blood flow through the parent vessel 10, as shown in FIG. 1A. FIG. 1B illustrates one embodiment of a monolithic device, shown next to a penny for general context as to size. As shown in FIG. 1C, the monolithic device may be bent along its longitudinal axis to conform to the shape or curvature of a blood vessel. After being deployment and bending along its longitudinal axis, the monolithic device 100 may be retrievable.

Figure 2:
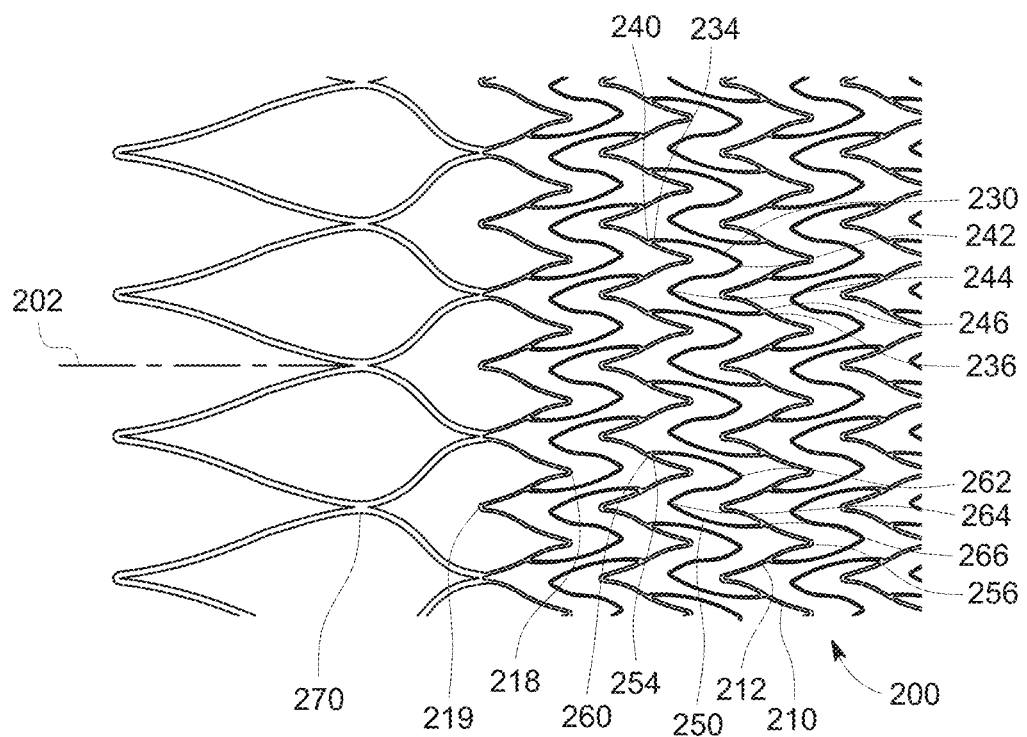
FIG. 2 illustrates one embodiment having mid-strut outer connections.

FIG. 2 illustrates one embodiment having mid-strut outer connections. The device 200 includes main body members 210 and bridge members 230, 250. Bridge members 230 are less stiff than bridge members 250. Main body members 210 comprise a plurality of struts 212. In some embodiments, the main body members 210 may comprise a Z pattern. The Z pattern may form a plurality of peaks 218 and a plurality of troughs 219 along the longitudinal axis 202. The bridge members 230 may comprise a first end 240 connected at 234 to a strut 212 of a first main body member 210, a first loop 242 facing a first end of the device 200, a second loop 244 connected to the first loop 242 and facing a second end of the device 200 in the opposite direction of the first loop 242, and the second loop 244 ending at a second end 246 that is connected at 236 to a strut 212 of an adjacent second main body member 210. The bridge members 250 may comprise a first end 260 that is connected at 254 to a strut 212 of a first main body member 210, a first loop 262 facing a first end of the device 200, a second loop 264 connected to the first loop 262 and facing a second end of the device 200 in the opposite direction of the first loop 262, and the second loop 264 ending at a second end 266 that is connected at 256 to a strut 212 of an adjacent second main body member 210. In some embodiments, the bridge members 250 have a greater width than bridge members 230. The device 200 may further comprise end body member 270.

The main body members 210 may comprise tight Z patterns, which allow the monolithic device 200 to maintain adequate radial force despite its small size. The interior cell structure may be modified to optimize performance.

The spacing between the bridge members 230, 250 as installed in the target vessel may be maintained between about 30 microns to limit blood flow into the aneurysm, alternatively, the spacing may be between 0.1-100.0 microns. The monolithic device 200 is able to bend, while the thickness of the monolithic device 200 may be between about 0.1-100.0 microns.

In one embodiment, the struts 212 may have a 20 micron width. In one embodiment, the bridges 230 may have a 12 micron width. In one embodiment, the bridges 250 may have a 24 micron width. In one embodiment, the bridges 250 may have an 18 micron width.

In some embodiments, the monolithic device 200 may be crimped around a guide wire. The crimping may collapse the main body members 210, the end body member 270, and the bridge members 230, 250 to a diameter between about 0.2 mm and about 2.0 mm. After the monolithic device 200 is uncrimped, the monolithic device 200 may expand to a diameter between about 2.0-7.0 mm while maintaining adequate radial force and wall apposition. In one embodiment, the thickness of the monolithic device is less than about 75 microns.

A radiopaque layer of Tantalum may be between two layers of metal for the monolithic device 200. Alternatively the Tantalum layer can be a top of bottom layer over a bottom layer of Nitinol, or Tantalum can be a bottom layer under a layer of Nitinol. Other embodiments may include other radiopaque materials other than Tantalum, or multiple layers of various materials (e.g. a five layer structure with Tantalum layers near the outer layers to minimize the impact of the Tantalum on the mechanical performance by moving the Tantalum away from the high strain regions of the cross section).

In some embodiments, hinge regions of the bridge members may be keyholed.

Figure 3:
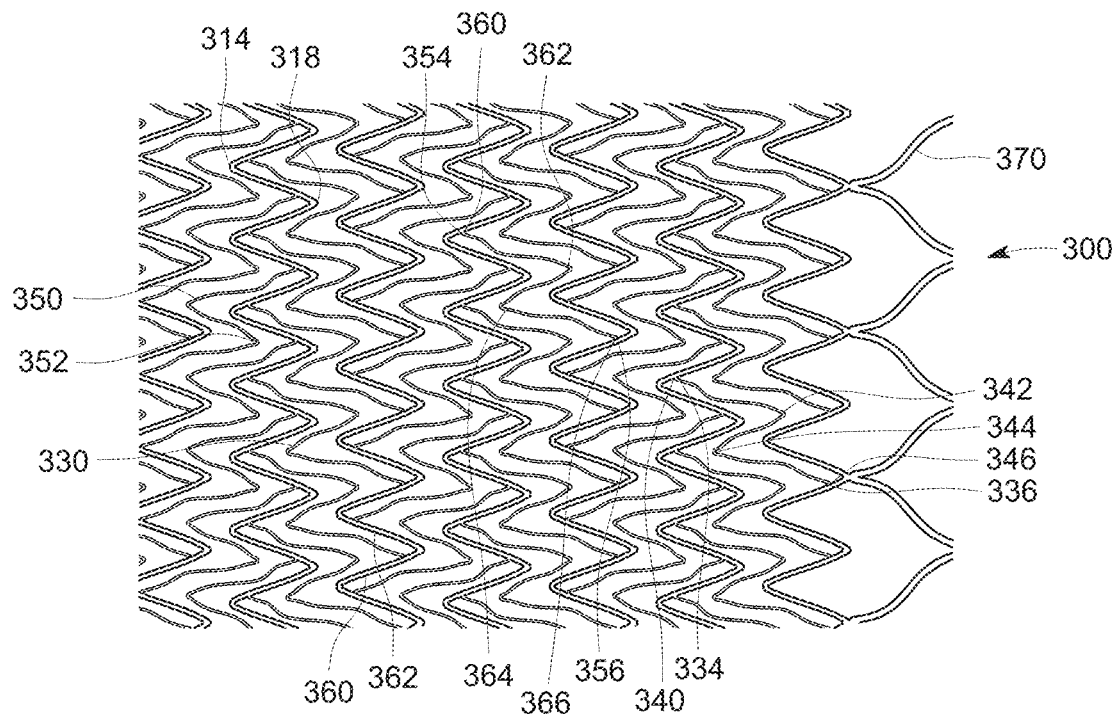
FIG. 3 illustrates one embodiment having mid-strut outer opposite connections.

FIG. 3 illustrates one embodiment having mid-strut outer opposite connections. The device 300 includes main body members 310 and bridge members 330, 350. Bridge members 330 are less stiff than bridge members 350. Main body members 310 comprise a plurality of struts 312. In some embodiments, the main body members 310 may comprise a Z pattern. The Z pattern may form a plurality of peaks 318 and a plurality of troughs 319. The bridge members 330 may comprise a first end 340 connected at 334 to a strut 312 of a first main body member 310, a first loop 342 facing a first end of the device 300, a second loop 344 connected to the first loop 342 and facing a second end of the device 300 in the opposite direction of the first loop 342, and the second loop 344 ending at a second end 346 that is connected at 336 to a strut 312 of an adjacent second main body member 310. The bridge members 350 may comprise a first end 360 that is connected at 354 to a strut 312 of a first main body member 310, a first loop 362 facing a first end of the device 300, a second loop 364 connected to the first loop 362 and facing a second end of the device 300 in the opposite direction of the first loop 362, and the second loop 364 ending at a second end 366 that is connected at 356 to a strut 312 of an adjacent second main body member 310. The bridge members 350 may further comprise nipples 352 at the tips of the first and second loops 362, 364. The nipples 352 may aid in folding of the device 300 for crimping. In some embodiments, the bridge members 350 have a greater width than bridge members 330. The device 300 may further comprise end body member 370.

The mid-strut connections may be used in the monolithic devices to minimize the bending of the body members by the bridges. The mid-strut connections also increase the coverage of the monolithic devices.

Figure 4:
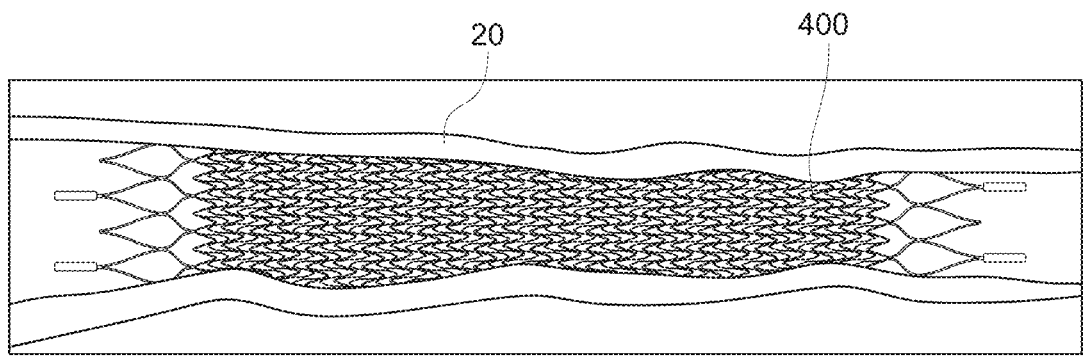
FIG. 4 illustrates one embodiment demonstrating the improved conformability of the monolithic stents.

FIG. 4 illustrates one embodiment demonstrating the improved conformability of the monolithic stents. One embodiment of an monolithic stent 400 is shown demonstrating a high degree of conformability to a vessel 20, where the vessel 20 has a non-uniform structure.

Figure 5A:
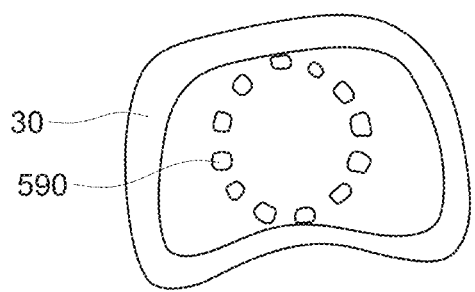
FIG. 5A shows the general conformability of a braided stent in an end view of a non-circular artery.
Figure 5B:
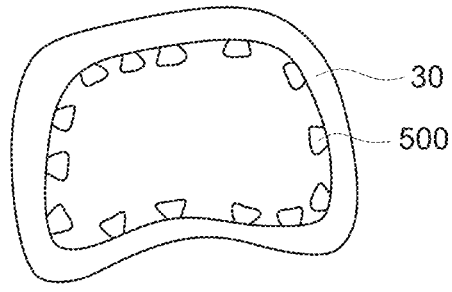
FIG. 5B shows the general conformability of embodiments of the monolithic stents, in an end view of a non-circular artery.
Figure 5C:
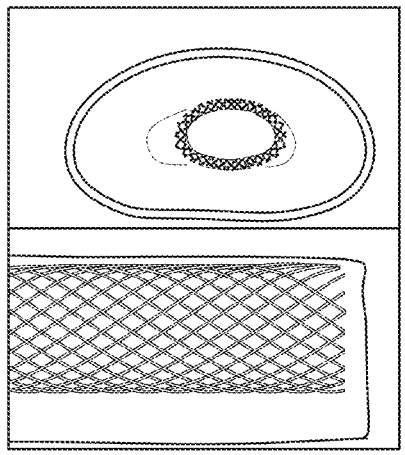
FIGS. 5C and 5D show end and top views of braided stents (FIG. 5C) and the monolithic stents (FIG. 5D) in a non-circular vessel.
Figure 5D:
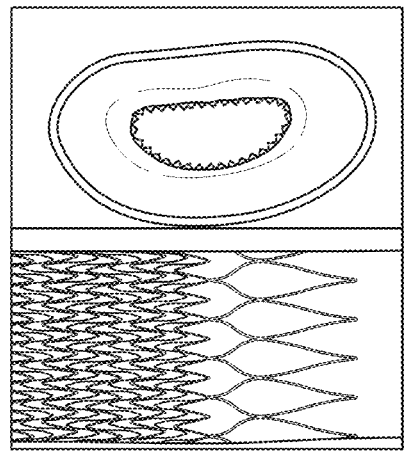

FIG. 5A shows the general conformability of a braided stent 590 in an end view of a non-circular artery 30. As can be seen, braided stents do not exhibit a high degree of conformability to non-circular arteries 30. FIG. 5B shows the general conformability of embodiments of the monolithic stents 500 in an end view of a non-circular artery 30. As can be seen, the monolithic stents 500 exhibit a high degree of conformability to non-circular arteries 30. FIGS. 5C and 5D show end and top views of braided stents (FIG. 5C) and the monolithic stents (FIG. 5D) in a non-circular vessel, to show the degree of conformability of the different devices. As can be plainly seen, the monolithic stents have a much higher degree of conformability to non-circular vessels than braided stents.

FIG. 6 illustrates one embodiment utilizing strut tapering. Tapering may be applied to the struts of a main body member between a connection point with a bridge member and a peak or trough point of the body member. Tapering does not significantly alter the stent's radial force or peak strain, but allows for lower crimp profiles.

Figure 7:
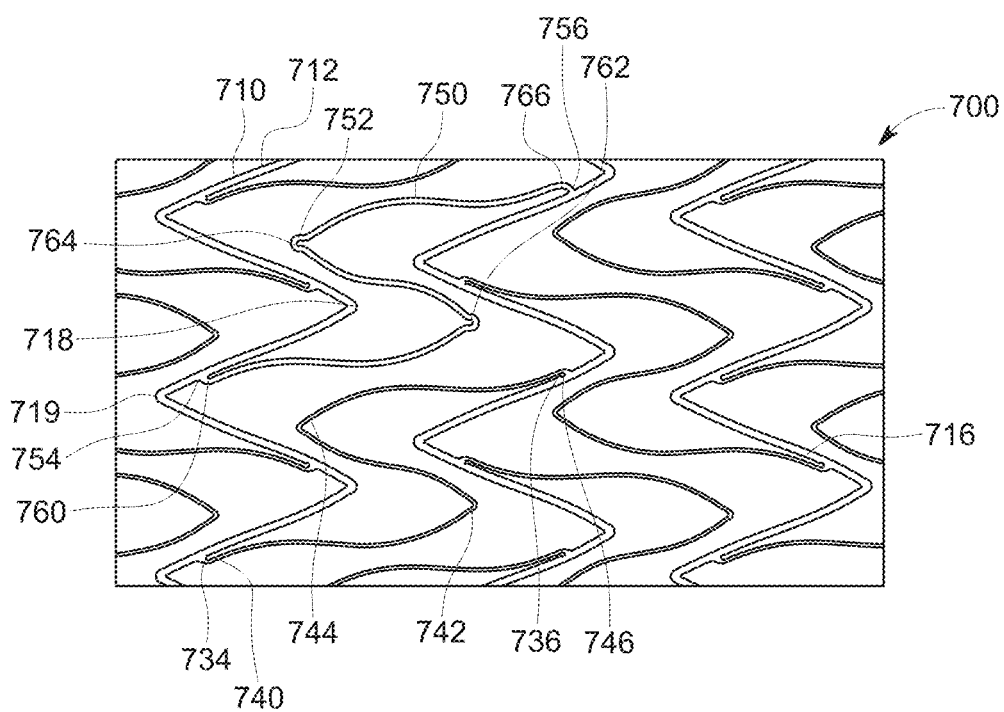
FIG. 7 illustrates one embodiment having undercuts (keyholing).

FIG. 7 illustrates one embodiment having undercuts (keyholing). In FIG. 7, the struts are tapered, and the stiff bridges (red) include nipples at the tips.

FIG. 7 illustrates an embodiment of the device 700. The device 700 includes main body members 710 and bridge members 730, 750. Bridge members 730 are less stiff than bridge members 750. Main body members 710 comprise a plurality of struts 712. In some embodiments, the main body members 710 may comprise a Z pattern. The Z pattern may form a plurality of peaks 718 and a plurality of troughs 719. The struts 712 of the main body members 710 may further include tapering 716. The bridge members 730 may comprise a first end 740 connected at 734 to a strut 712 of a first main body member 710, a first loop 742 facing a first end of the device 700, a second loop 744 connected to the first loop 742 and facing a second end of the device 700 in the opposite direction of the first loop 742, and the second loop 744 ending at a second end 746 that is connected at 736 to a strut 712 of an adjacent second main body member 710. The bridge members 750 may comprise a first end 760 that is connected at 754 to a strut 712 of a first main body member 710, a first loop 762 facing a first end of the device 700, a second loop 764 connected to the first loop 762 and facing a second end of the device 700 in the opposite direction of the first loop 762, and the second loop 764 ending at a second end 766 that is connected at 756 to a strut 712 of an adjacent second main body member 710. The bridge members 750 may further comprise nipples 752 at the tips of the first and second loops 762, 764. The nipples 752 may aid in folding of the device 700 for crimping. In some embodiments, the bridge members 750 have a greater width than bridge members 730. The connection points 734, 736, 754, 756 in FIG. 7 show exemplary undercutting or keyholing between the bridge members 730, 750 and the body members 710.

Figure 8:
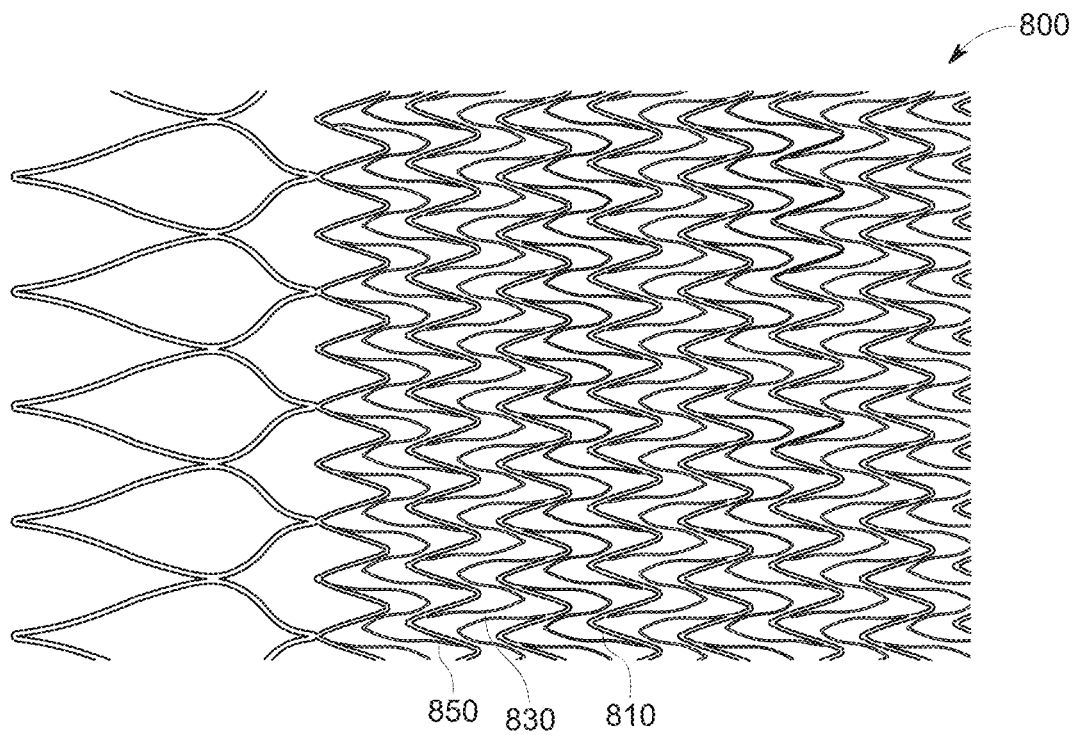
FIG. 8 illustrates a high density twenty crown design device with mid-strut outer connections, showing coverage density.

FIG. 8 illustrates a high density twenty crown design device 800 with mid-strut outer connections, showing coverage density. The device 800 may comprise main body members 810, and bridge members 830, 850. Bridge members 830 may be less stiff than bridge members 850.

Figure 9:
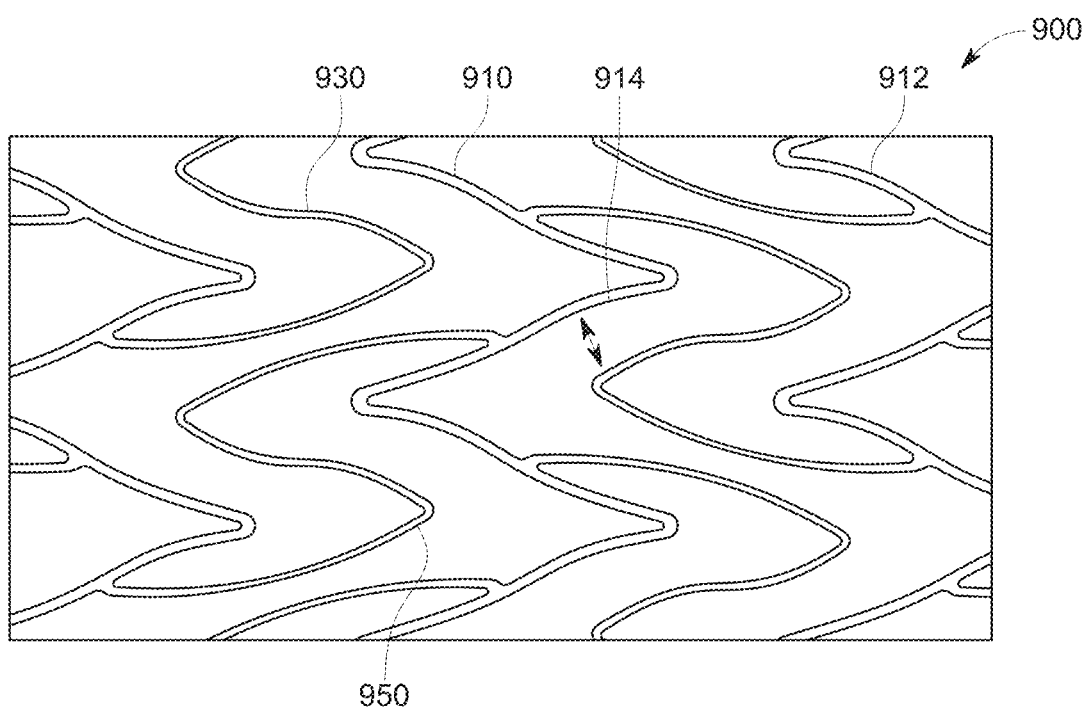
FIG. 9 illustrates distortion of struts to accommodate bridge features when the device is crimped.

FIG. 9 illustrates distortion of struts to accommodate bridge features when the device 900 is crimped. The struts 912 of main body members 910 may be distorted, such as in region 914, to accommodate the bridge members 930, 950. In some embodiments, bridge members 930 may be less stiff than bridge members 950.

Figure 10:
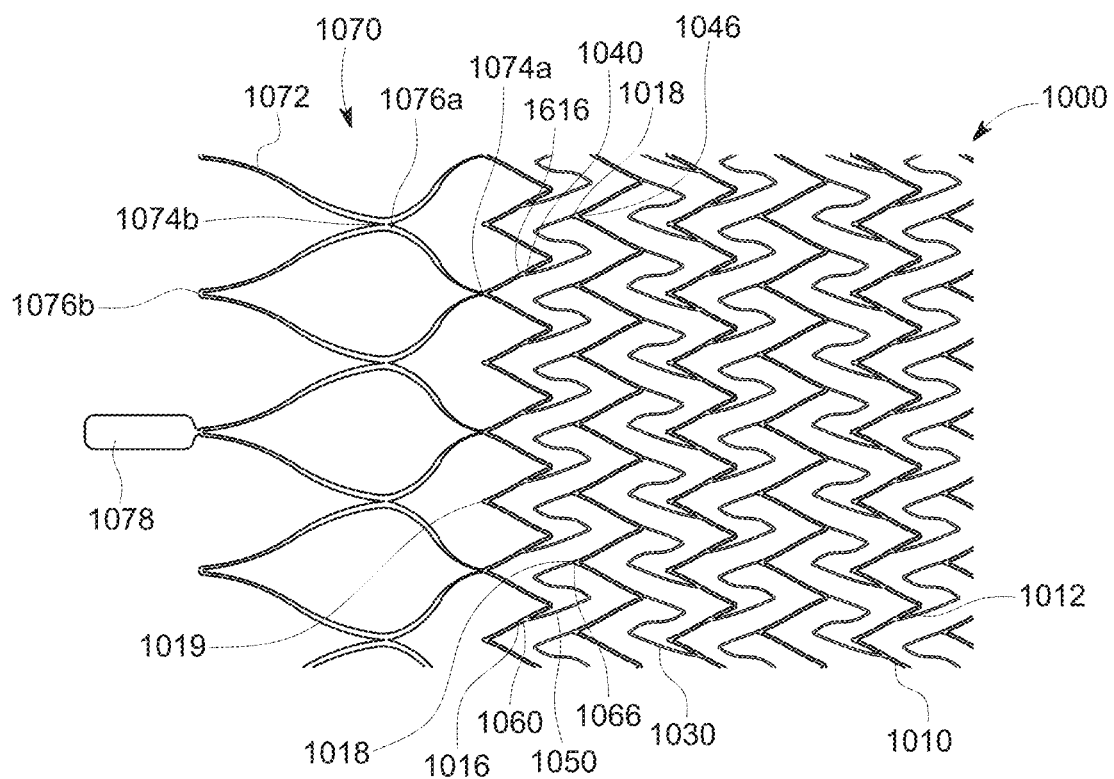
FIG. 10 illustrates a hybrid bridge connection from tip to mid-strut, as well as one embodiment of end geometry for anchoring and/or flaring.

FIG. 10 illustrates a hybrid bridge connection from tip to mid-strut, as well as one embodiment of end geometry for anchoring and/or flaring. As shown in FIG. 10, a device 1000 may include main body members 1010 and bridge members 1030, 1050. Bridge members 1030, 1050 may be connected at a first end 1040, 1060 to a midpoint 1016 of a strut 1012 of a first main body member 1010, and connected at a second end 1046, 1066 to a tip 1018 of an adjacent second main body member 1010. FIG. 10 further illustrates an embodiment of a device 1000 including an end body member 1070. The end body member 1070 may comprise a generally Z pattern of struts 1072, including a plurality of interconnected peaks 1074a and troughs 1076a. Optionally, the end body member 1070 may include additional interconnected peaks 1074b and troughs 1076b, whereby the peaks 1074b are to the troughs 1076a, as to further extend the end of the device 1000. In some embodiments, the end body member 1070 may further comprise attachment members 1078 connected to one or more troughs 1076b. Attachment members 1078 may be generally planar, generally rectangular, match a radius of curvature of device 1000, etc.

In one embodiment, the peak 1074a of the end body member 1070 connects to every other trough 1019 of the first main body member 1010, such that the peak 1074a of each end body member 1070 does not connect to adjacent troughs 1019 of the first main body member 1010. This connection forms a larger end body member Z pattern. In one embodiment, the peak 1074a of the end body member 1070 connects to every third trough 1019 of the first main body member 1010, while in other embodiments, the peak 1074a may connect to every fourth trough 1019 of the first main body member 1010. The modified end body members of the device geometry may prevent cell migration as well as be used for marker placement. Alternatively, the end body members may be modified or eliminated completely from the monolithic device.

Figure 11:
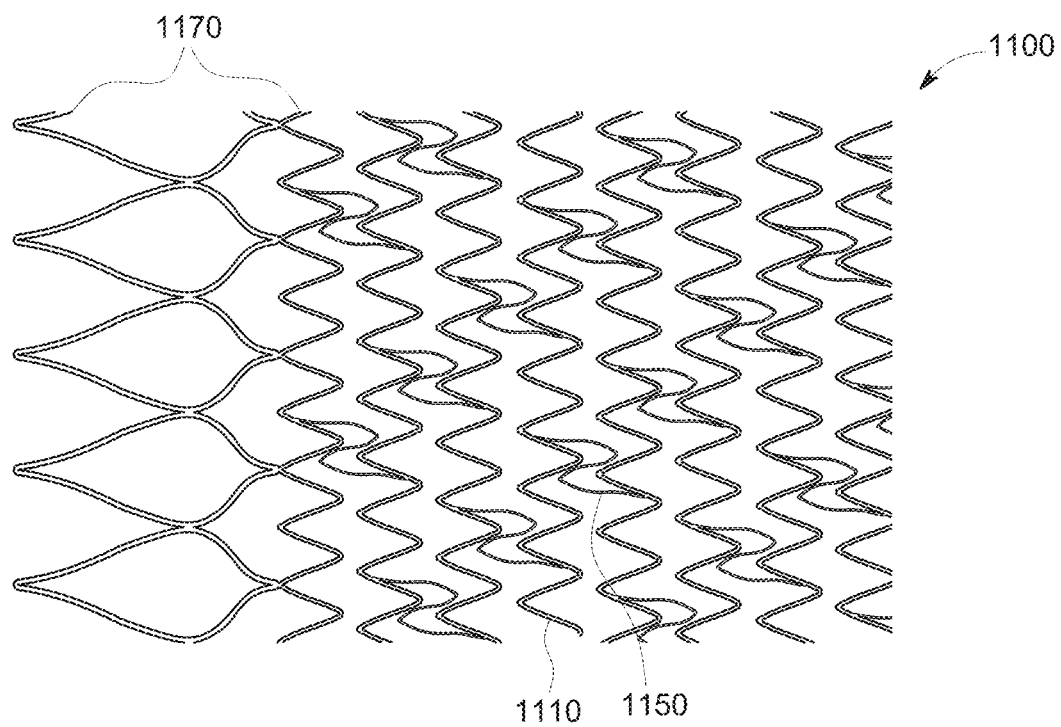
FIG. 11 illustrates one embodiment of a device having a sparse bridge pattern.

FIG. 11 illustrates one embodiment of a device 1100 having a sparse bridge pattern. The device 1100 may comprise main body members 1110 and bridge members 1150. In some embodiments, the device 1100 may further comprise an end body member 1170.

Figure 12:
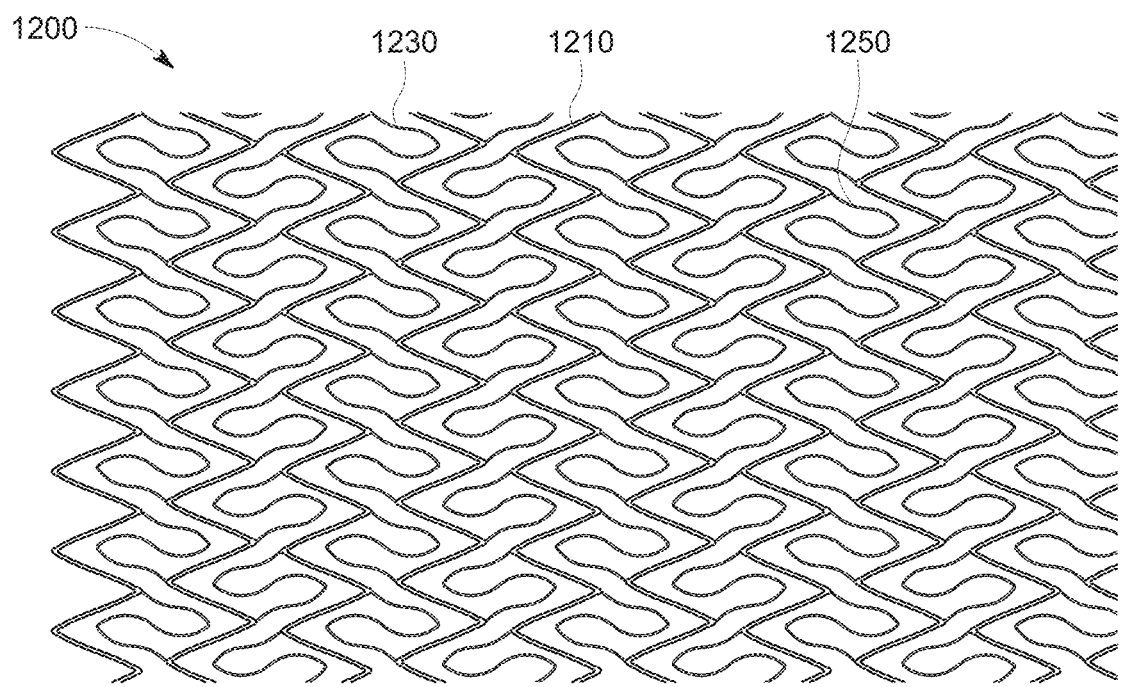
FIG. 12 illustrates one embodiment of a device having a potentially retrievable bridge geometry.

FIG. 12 illustrates one embodiment of a device 1200 having a potentially retrievable bridge geometry. The device 1200 may comprise main body members 1210 and bridge members 1230, 1250. Bridge members 1230 may be less stiff than bridge members 1250. Bridge members 1230, 1250 may be connected to tips of adjacent main body members 1210.

Figure 13:
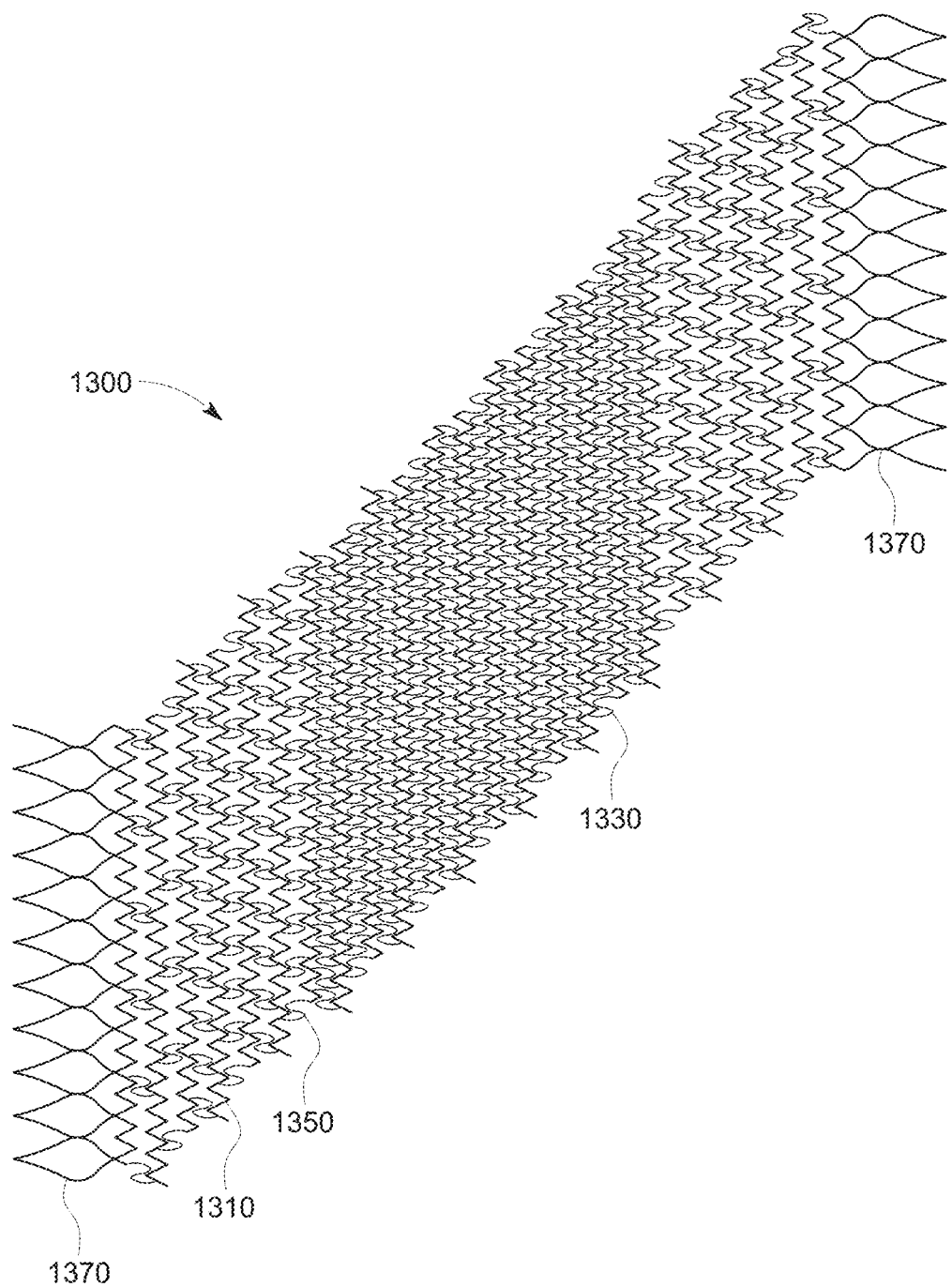
FIG. 13 illustrates one embodiment of a variable bridge pattern for localized parameter tuning.

FIG. 13 illustrates one embodiment of a variable bridge pattern for localized parameter tuning. The pattern 1300 may include main body members 1310 and bridge members 1330, 1350. Bridge members 1330 may be less stiff than bridge members 1350. The pattern 1300 may further include end body members 1370 at either end of the pattern 1300. As shown in FIG. 13, the pattern of bridge members 1330, 1350 between main body members 1310 may vary along the length of the pattern 1300, such as by varying in bridge member concentration from sparser, to denser, to sparser. This could be helpful for patches/containment or to gradually change the radial force or coverage toward the ends of the stent to allow for side branches of bifurcations.

Figure 14:
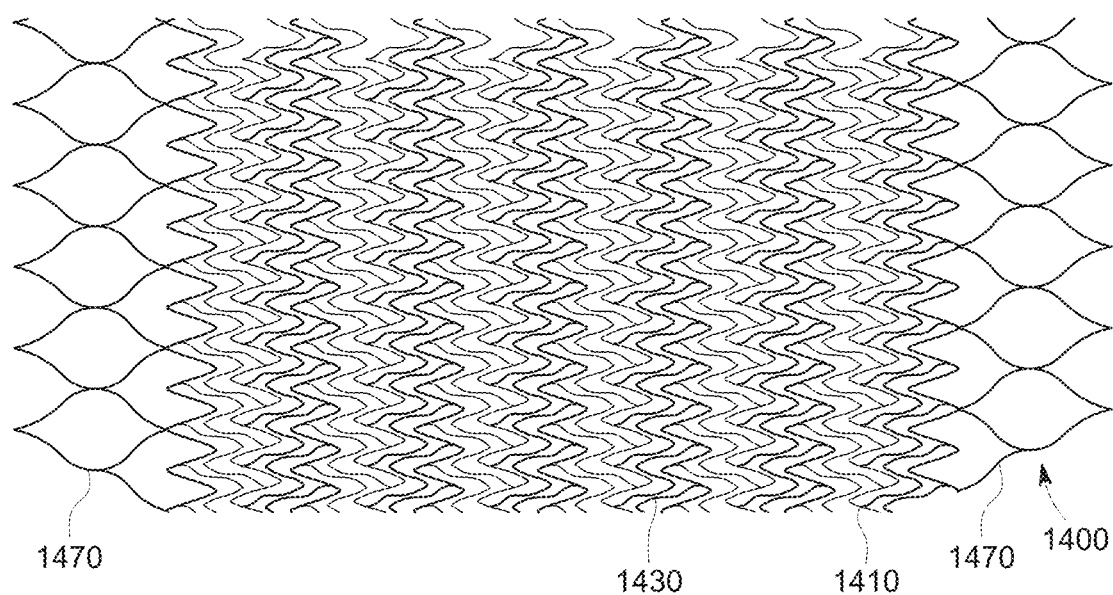
FIG. 14 illustrates one embodiment of a device having a twelve crown adjunctive pattern with identical mid-strut outer bridges, mirrored in alternating rows.

FIG. 14 illustrates one embodiment of a device 1400 having a twelve crown adjunctive pattern with identical mid-strut outer bridges, mirrored in alternating rows. The device 1400 may comprise end body members 1470, main body members 1410, and bridge members 1430.

Figure 15:
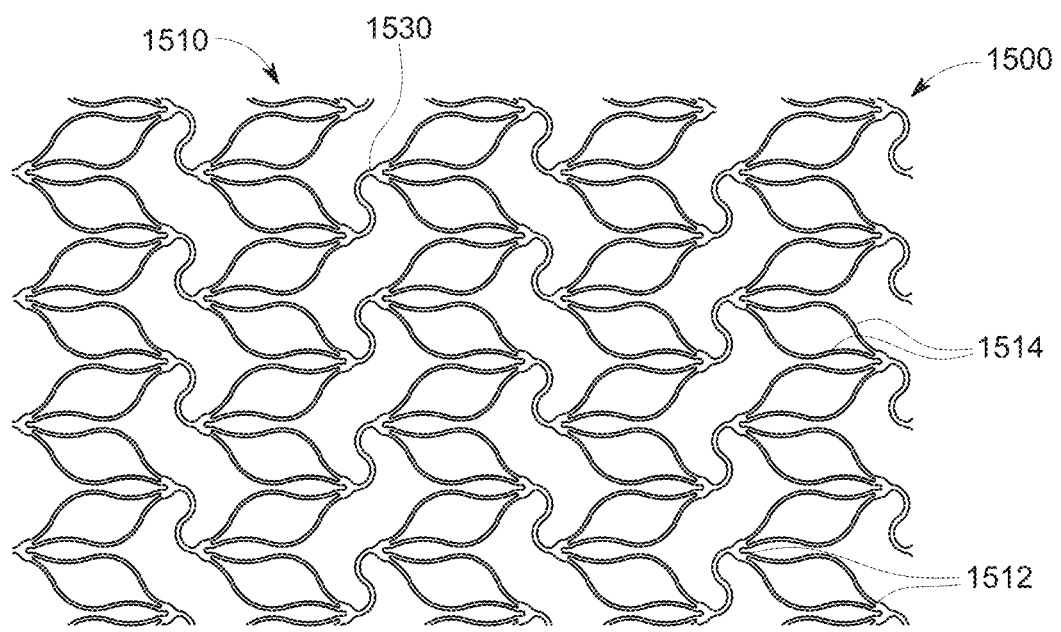
FIG. 15 illustrates an embodiment of a device having a split strut pattern.

FIG. 15 illustrates an embodiment of a device 1500 having a split strut pattern. The device 1500 may comprise main body members 1510 interconnected by bridge members 1530. Each main body member 1510 may comprise a generally Z pattern of segments 1512. Each segment 1512 is split into two struts 1514 between a peak and a trough of the Z pattern.

Figure 16:
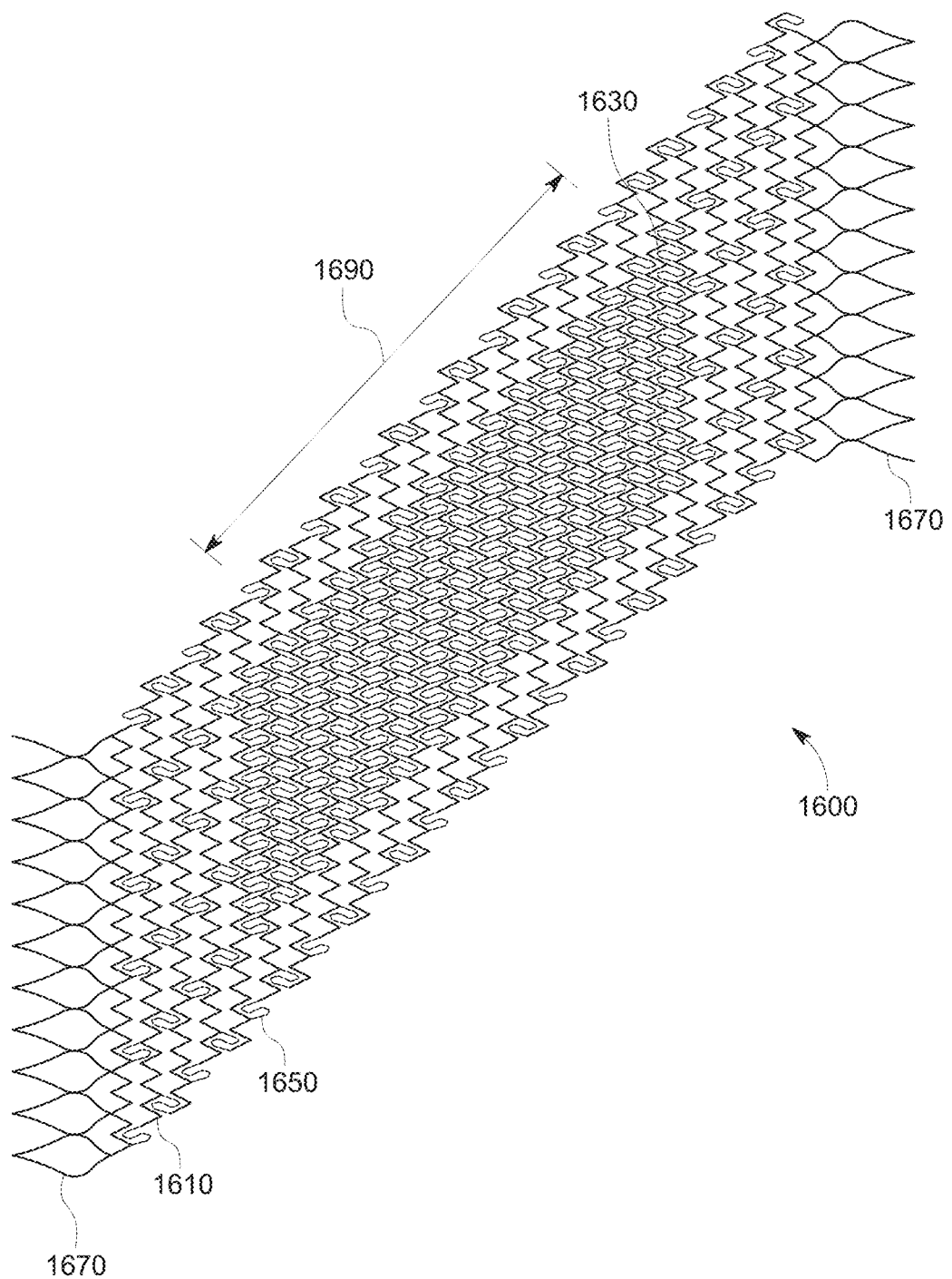
FIG. 16 illustrates one embodiment of a device having a pattern for use in a patch application, with a high density section.

FIG. 16 illustrates one embodiment of a device 1600 having a pattern for use in a patch application, with a high density section. The device 1600 may comprise end body members 1670, main body members 1610, and bridge members 1630, 1650. Bridge members 1630 may be less stiff than bridge members 1650. At least a portion 1690 of the device 1600 may have a high density section to prevent passage of fluids therethrough.

Figure 17A:
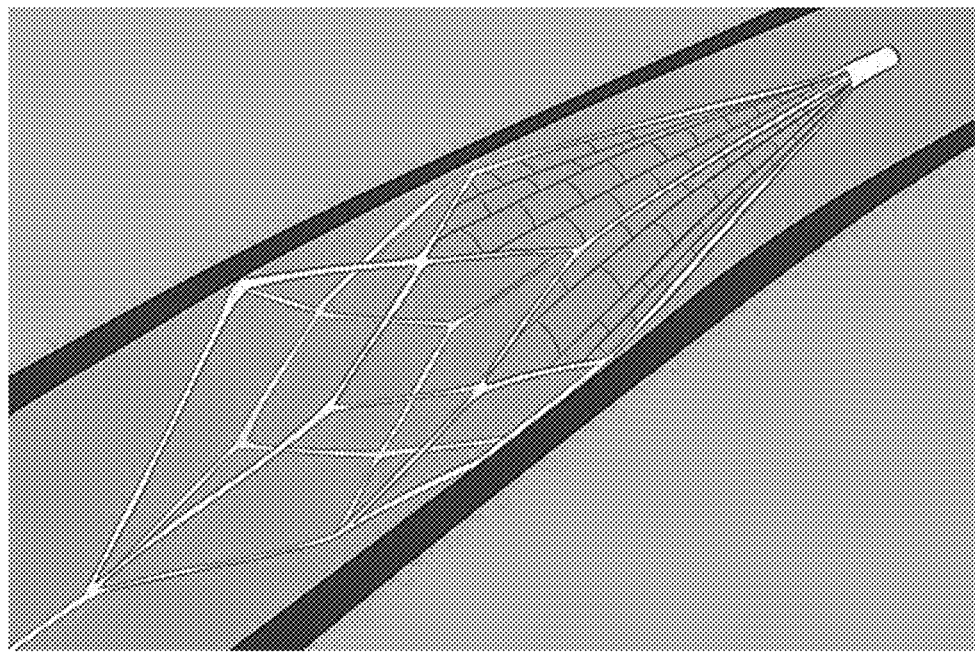
FIGS. 17A and 17B illustrate possible embodiments of devices for use as integral baskets or filters.
Figure 17B:
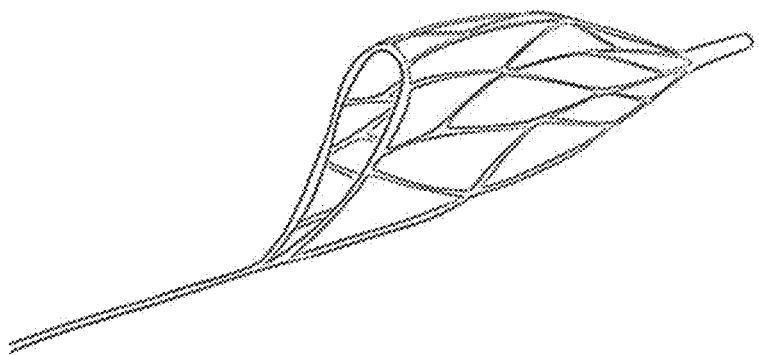

FIGS. 17A and 17B illustrate possible embodiments of devices for use as integral baskets or filters.

FIGS. 18A-D illustrate various views of one embodiment of a device for clot retrieval. FIG. 18A illustrates a side view of a device 1800 for clot retrieval, wherein the members of the device have a generally wedge cross section that is smaller at the outer surface of the device than at the inner surface of the device. FIG. 18B shows an end view of the device 1800 in a crimped state. FIG. 18C shows an end view of the device 1800 expanded within a body vessel. FIG. 18D shows an enlarged end view of a generally wedge cross section strut 1812 embedding into the vessel wall. In some embodiments, the generally wedge shape may aid penetration and anchoring in a vessel.

The methods of making implantable medical devices include vapor deposition. In some embodiments, vapor deposition may be used to form deposited initial tubes or films on a substrate. The tubes or films can be fabricated at the expanded size of the resultant device, meaning no expansion post-formation is necessary. This eliminates the heat treatment, preserves the material properties, and eliminates the need to remove heat treatment oxides and residues. Since the deposition process deposits the device forming material on a stable, stiff substrate material, this substrate can stay in place during cutting, preventing material relaxation and allowing tighter tolerances, smaller features, and simplified laser toolpath generation. Cutting using athermal ablation eliminates the heat affected zone, dross and splatter associated with heat cutting.

The laser cut part can be electropolished while still on the substrate with the electropolish anode contact at the ID of the substrate tube or film. This eliminates any concerns about contact marks since the substrate will be removed later. This also keeps the current density uniform for uniform material removal. Since there is no heat affected zone to remove and the deposited tube or film surface is very smooth, the typical material removal is only 2-3 microns per surface. The reduced material removal improves process control, feature uniformity, and results in longer electropolish chemical bath life.

Finally, the device is separated from the substrate by submersion in an acid bath which selectively dissolves the substrate material away leaving the finished device.

In some embodiments, some of the advantages may be imparted wrought materials rather than deposited materials, by filling the inner diameter of a wrought tube with solidified salt or a low melting point metal or the like to be removed later, such that the advantages of the substrate of the present method may be afforded to the wrought tube.

The methods of making implantable medical devices include vapor deposition. In some embodiments, vapor deposition may be used to form deposited initial tubes or films on a substrate. The tubes or films can be fabricated at the expanded size of the resultant device, meaning no expansion post-formation is necessary. This eliminates the heat treatment, preserves the material properties, and eliminates the need to remove heat treatment oxides and residues. Since the deposition process deposits the device forming material on a stable, stiff substrate material, this substrate can stay in place during cutting, preventing material relaxation and allowing tighter tolerances, smaller features, and simplified laser toolpath generation. Cutting using athermal ablation eliminates the heat affected zone, dross and splatter associated with heat cutting.

The laser cut part can be electropolished while still on the substrate with the electropolish anode contact at the ID of the substrate tube or film. This eliminates any concerns about contact marks since the substrate will be removed later. This also keeps the current density uniform for uniform material removal. Since there is no heat affected zone to remove and the deposited tube or film surface is very smooth, the typical material removal is only 2-3 microns per surface. The reduced material removal improves process control, feature uniformity, and results in longer electropolish chemical bath life.

Finally, the device is separated from the substrate by submersion in an acid bath which selectively dissolves the substrate material away leaving the finished device.

In some embodiments, some of the advantages may be imparted wrought materials rather than deposited materials, by filling the inner diameter of a wrought tube with solidified salt or a low melting point metal or the like to be removed later, such that the advantages of the substrate of the present method may be afforded to the wrought tube.

Generally speaking, the devices comprise monolithic, single component devices. For example, and without limitation, a monolithic stent device differs from known covered stents which have two primary components—a base stent and a fine mesh cover—which are then joined together. The single component devices may be used in similar applications to known covered devices, but use a single component to generate bulk and fine features simultaneously. In some embodiments, the monolithic devices may have a lower profile as compared to covered devices, because in the monolithic devices both structures occupy the same layer.

In some embodiments, the monolithic device may be generated by laser machining. In some embodiments, the monolithic device may be generated by photolithography or other selective etching methodologies. In some embodiments, the monolithic device may be generated by PVD overgrowth, wherein material is vapor deposited over a base device geometry, then the mesh pattern is cut or etched. In some embodiments, the monolithic device may be generated flat and then formed into a tube. In some embodiments, the monolithic device may be generated from a tube and then formed into a different radius or flattened, or may be formed into another desired shape.

In some embodiments, the monolithic devices may include integral RO enhancement via doping and/or layering. In some embodiments, the devices may be supplemented with the addition of markers. In some embodiments, the devices may further comprise paddles or thicker struts added to the mesh geometry throughout the length of the device to aid in imaging visibility. In some embodiments, the monolithic devices may utilize a superposition of strong body and weaker mesh structure. In these embodiments, the rows of main body members may provide the primary radial force, while the bridge members may provide flexibility, conformability, integration (such that the device acts as a single unit), and axial stiffness.

In some embodiments, the pattern of bridge members may be varied in population to adjust coverage, compliance, stiffness, and/or the like. In some embodiments, extra features, such as whiskers or redundant bridges or the like, may be added to fill additional open spaces in the device. In some embodiments, redundant bridges may act as non-compliant bridges for axial stiffness. In some embodiments, the monolithic devices may further comprise flared ends. The flared ends may provide anchoring and improve the device's ability to adapt to curved anatomies.

Generally, the high density of the monolithic devices has benefits for low wall stress, flow diversion, plaque containment, and/or the like. In some embodiments, the monolithic devices have low foreshortening, which aids placement accuracy and sizing. Low foreshortening also minimizes the metal content as the final device length is predictable. In some embodiments, the high element count reduces alternating strains in the monolithic devices, resulting in high fatigue resistance. In some embodiments, the bridge geometry of the monolithic devices may be designed to rotate during stretching, so as to provide improved pattern density in the outside of a bend.

In some embodiments, the bridge geometry of the monolithic devices may be designed to interlock during stretching to limit expansion in the outside of a bend, thereby increasing flow diversion and limiting expansion into an aneurysm or other cavity. In some embodiments, the bridge members may further be designed to contact one another in the vessel loaded position, so as to further decrease the pore size of the monolithic devices.

In some embodiments, the bridge geometry of the monolithic devices may be designed to fold inward, thereby filling more interior space and allowing for lower cannula diameters. In some embodiments, this inward folding may be accomplished by designing bridge members that spontaneously fold inward, or by folding the bridge members inwards while crimping the device (such as in known balloon catheter folding techniques).

In some embodiments, the monolithic devices may have a varying pattern and/or ratio of bridge stiffnesses. This varying pattern and/or ratio may add backbone to the device for kink resistance, stretch resistance, axial stiffness, conformability, and/or the like. In some embodiments, the pattern may be within rows. In some embodiments, the pattern may be varied across the device. A variety of stiff bridge patterns are possible, to allow for design tuning. For example, and without limitation, the stiff bridge pattern may be helical (at various pitch angles), diamond, staggered, random, and/or the like. The varied patterns may result in tapered radial force. Other patterns may vary the radial force and/or coverage of the monolithic devices.

In one embodiment, the making of implantable medical devices is by physical vapor deposition (PVD) and other embodiments, wrought pre-existing metal or polymer is used. In some embodiments, PVD (or other deposition methodologies) may be used to form deposited initial tubes on a substrate. The tubes can be fabricated at the expanded size of the resultant device, meaning no expansion post-formation is necessary. This eliminates the heat treatment, preserves the material properties, and eliminates the need to remove heat treatment oxides and residues. Since the PVD process deposits the device forming material on a stable, stiff substrate material, this substrate can stay in place during cutting, preventing material relaxation and allowing tighter tolerances, smaller features, and simplified laser toolpath generation. Cutting using athermal ablation eliminates the heat affected zone, dross and splatter associated with heat cutting. A femtosecond or other athermal laser may be used to ablate the geometry through the device forming deposited material layer, leaving the substrate largely intact.

The methods disclosed herein impart numerous advantages over the prior art. Generally, the advantages of the present method include: fewer and simpler steps than in wrought processing; fewer steps are easier and faster to validate, improving time to market; tighter tolerances and more intricate features are possible; material properties retained means higher properties or less material needed to generate required forces (e.g. radial force); lower cost and higher yields; reduced labor content; higher process yields due to simplified process and micro feature capability; methods are amenable to automation due to substrate presence until the final processing steps; PVD material has intrinsically tighter tolerances and higher properties than wrought materials (also allow for alloying additions for enhanced material properties, radiopacity, etc.); PVD allows for much lower OD/ID ratios than are possible by drawing; PVD allows for non-cylindrical tubing (rectangular box, corrugated, tapered, variable diameter, etc.); smaller feature sizes afforded by laser beam size and minimized material removal allow for smaller profile as the dimensional stack is reduced; tighter tolerances means less device output variation and easier product verification.

Figure 19:
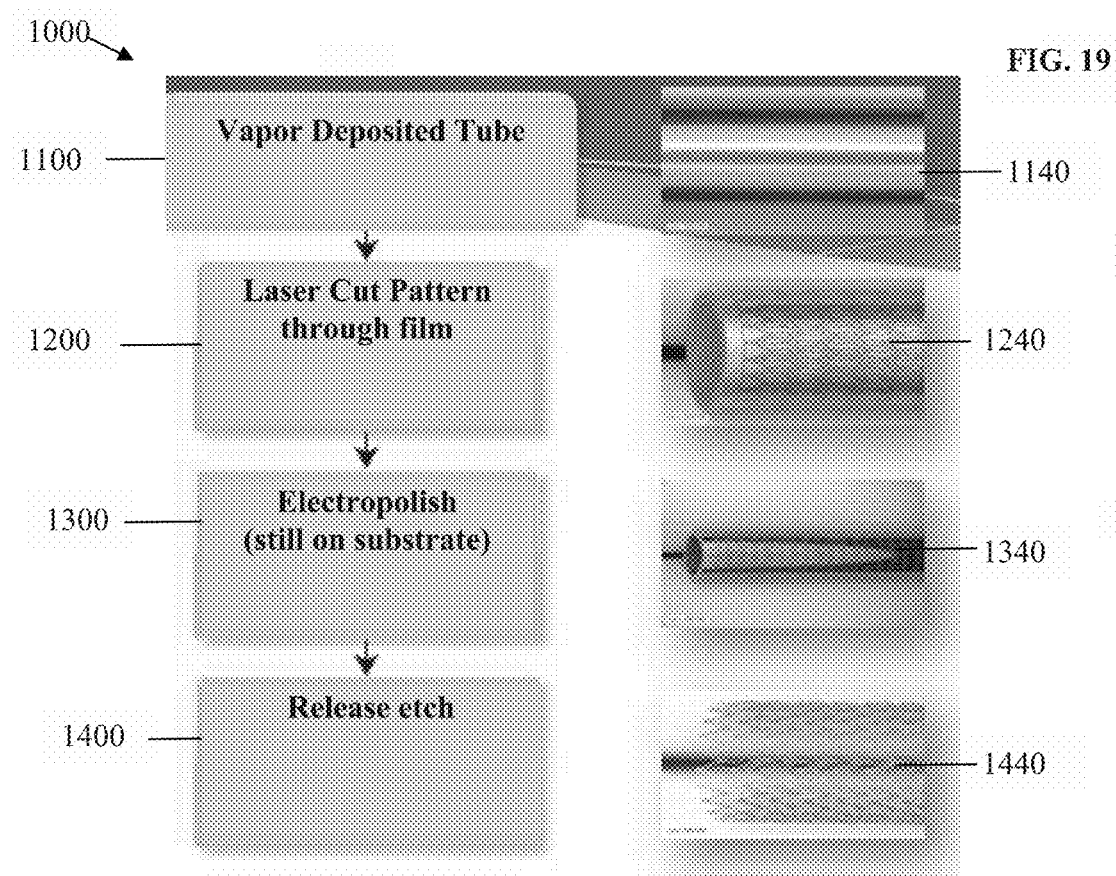
FIG. 19 is a general flow chart of one embodiment of a method of making medical devices.
Figure 20:
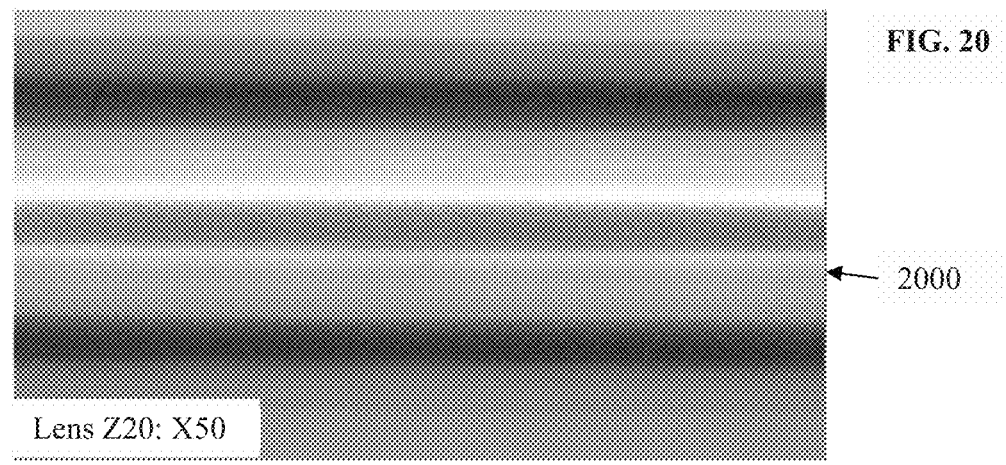
FIG. 20 shows an enlarged view of a portion of an as-deposited tube.

FIG. 19 is a general flow chart of one embodiment of a method 1000 of making monolithic devices. In some embodiments, an initial tube or film is vapor deposited (1100) onto a substrate. One embodiment of a vapor deposited initial tube 2000 is shown at 1140 and FIG. 20. After the initial tube or film is prepared, the tube or film may be imparted with a laser cut pattern through the tube or film (1200), while the tube or film is still on the substrate. One embodiment of a tube with a laser cut pattern is shown at 1240 and FIG. 21. After the laser cut pattern is imparted, the patterned tube or film may be electropolished (1300) while still on the substrate. One embodiment of an electropolished patterned tube still on a substrate is shown at 134 and FIG. 25. Finally, the patterned and electropolished device may be separated from the substrate (1400), such as by a release etch. In some embodiments, the device is released from the substrate by immersion in an acid bath which selectively dissolves the substrate material while leaving the finished device unaltered. One embodiment of a finished device released from a substrate is shown at 1440.

In some embodiments, the initial tube or film may be a wrought metal, polymer, composite, or ceramic tube or film, or may be vacuum deposited metal or polymer tube or film. The deposition procedure may be employed by commonly assigned U.S. patent application Ser. No. 13/788,081, filed Mar. 7, 2013 or in U.S. patent application Ser. No. 13/099,980, filed May 3, 2011, herein incorporated by reference in their entireties. Alternatively, the device may be produced from drawn metal or polymer tubing, or wrought tubing, provided that fatigue life is adequate. Radiopaque markers may be added as an interdispersed deposited layer or a ternary alloy deposition (e.g. NiTiTa or NiTiNb) if vacuum deposition is used. Different metal layers may be used to form the device. The positioning of the layers can be optimized for mechanical or other reasons. Furthermore, ternary additions to binary Nitinol can be used to strengthen or otherwise alter the material properties, allowing for lower profile devices, enhanced fatigue resistance, etc. These ternary additions can also double as radiopacity enhancers.

In an alternative embodiment, other deposition methodologies may be used to prepare the initial tube or film, including but not limited to chemical vapor deposition.

In some embodiments, the device is formed from a metal, a pseudometal, a polymer, a composite, or a ceramic material. In some embodiments, materials to make the stents are chosen for their biocompatibility, mechanical properties, i.e., tensile strength, yield strength, and their ease of deposition include, but are not limited to, the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel; and/or the like.

It is possible to support wrought materials and gain some of the process benefits afforded by the substrate of the present method by filling an initial wrought tube with solidified salt or a low melting point metal (or the like) to be removed later, and proceeding with the method 1000 from step 1200. Other substrate materials may also be used, provided they may be easily separated from the formed device at a later stage in the method.

In the method, devices may be formed at their expanded size, avoiding the need for post-formation expansion. This also may eliminate the need for heat treatment, may preserve the material properties, and may eliminate the need to remove oxides and residues resultant from heat treatment.

In some embodiments, heat treatment techniques may be used to tune material properties prior to the laser cutting step. For example, and without limitation, the present method may, in some embodiments, still allow for the formed devices to be expanded or shapeset into a different configuration after the device is released from the substrate. In some embodiments, Nitinol-based devices can be flared or otherwise reshaped by plastic deformation above the Md (Martensite deformation) temperature. Above Md, the material behaves as an elastic-plastic material. Stent end flaring has been accomplished by this means. The advantage of this method is that no significant oxide layer is formed and the material properties remain intact.

Figure 21:
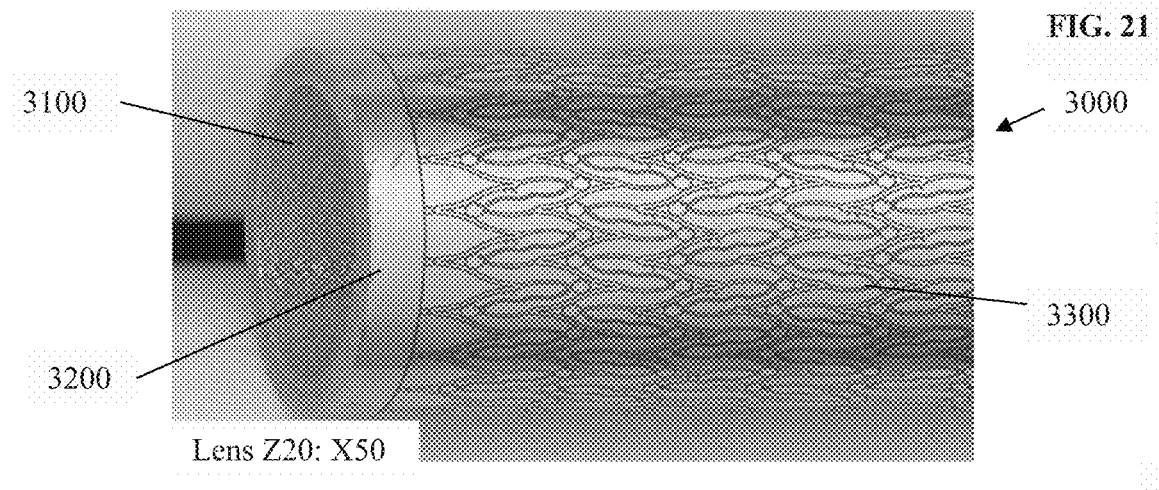
FIG. 21 shows one embodiment of an initial deposited tube on a substrate, with a laser cut (ablated) pattern imparted to the deposited tube.

Since the PVD process deposits the device forming material on a stable, stiff substrate material, this substrate can stay in place during cutting, preventing material relaxation and allowing tighter tolerances, smaller features, and simplified laser toolpath generation. FIG. 21 shows one embodiment 3000 of an initial deposited tube 3200 on a substrate 3100, with a laser cut pattern 3300 imparted to the deposited tube 3200.

In some embodiments, the laser cut pattern may be imparted using athermal ablation techniques. Athermal ablation eliminates the formation heat affected zones, dross, and splatter frequently associated with heat cutting. A femtosecond or other athermal laser may be used to ablate the device geometry through the initial film layer, leaving the substrate largely intact. These lasers also typically have smaller kerf widths, allowing for smaller features and inside radii.

Figure 22:
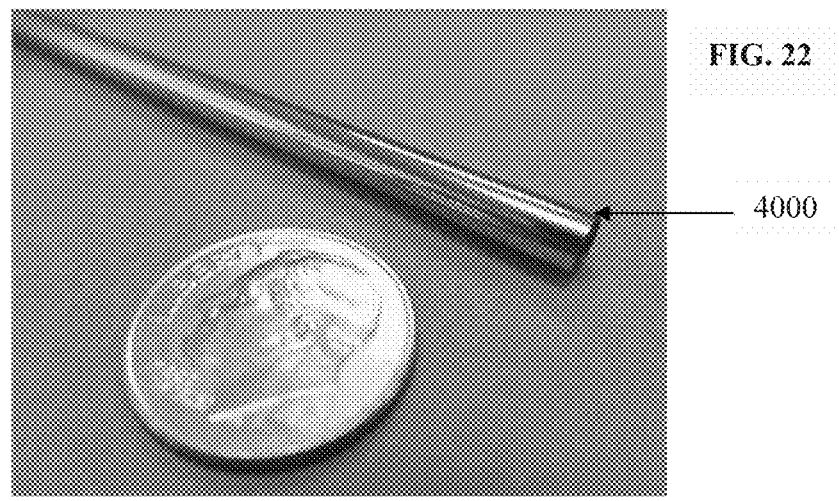
FIG. 22 shows an as-cut deposited tube on a substrate shown next to a standard dime for visual reference.
Figure 23:
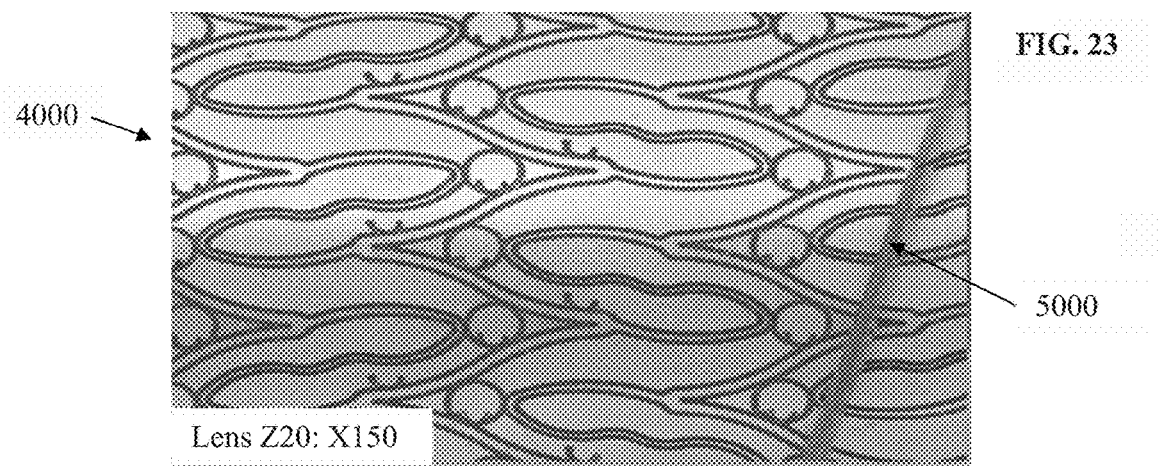
FIG. 23 shows an enlarged view of a portion of the as-cut deposited tube on a substrate of FIG. 22, with a human hair as a visual reference.

FIG. 22 shows an as-cut deposited tube on a substrate 4000 shown next to a standard dime for visual reference. FIG. 23 shows the same as cut deposited tube on a substrate 4000 with a human hair 5000 as a visual reference.

Figure 24:
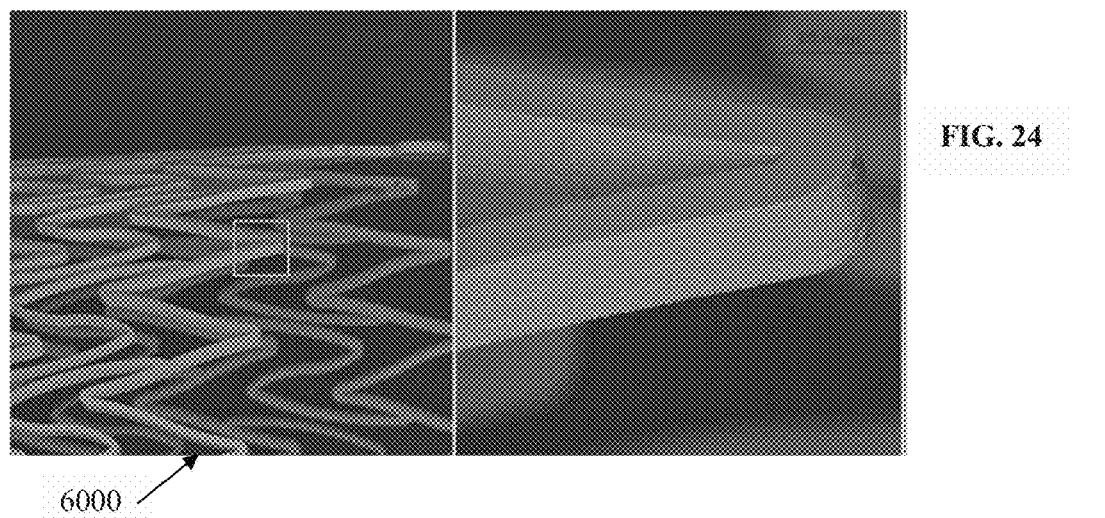
FIG. 24 shows a scanning electron microscopic image of a device formed by the present methods, showing the as-cut edge quality resultant from the present method.

FIG. 24 shows a scanning electron microscopic image of a device 6000 formed by the present method, showing the as-cut edge quality resultant from the present method.

In an alternative embodiment, other cutting methods, such as but not limited to EDM or waterjet may be substituted for laser ablation.

The laser cut part may be electropolished while still on the substrate with the electropolish anode contact at the inner diameter of the substrate tube or film. This eliminates any concerns about contact marks since the substrate will be removed later. This also keeps the current density uniform for uniform material removal. Since there is no heat affected zone to remove and the initial deposited tube or film surface is very smooth, the typical material removal during electropolishing is less than about 5 microns per surface, optimally only about 2 to about 3 microns per surface. Typical material removal during electropolishing is approximately 25 microns per surface. This reduced material removal improves process control, feature uniformity, and results in longer electropolish chemical bath life. In alternative embodiments, the formed components may be electropolished after removal from the substrate rather than while on the substrate. Still further, in some embodiments, the electropolishing step may be omitted if it is not necessary for the device being produced.

Figure 25:
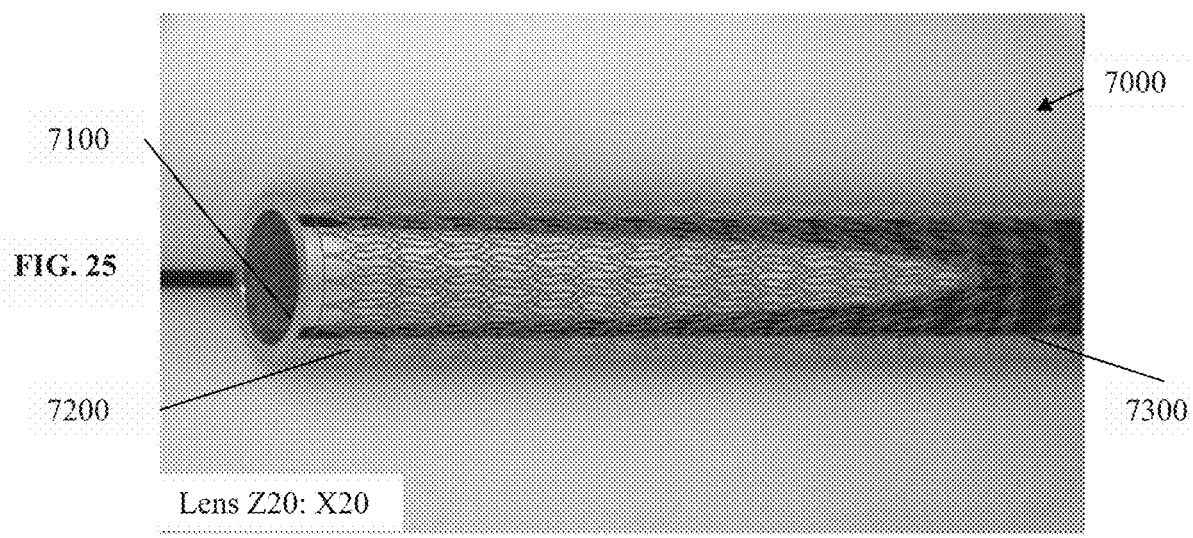
FIG. 25 shows the deposited film/tube on the substrate, with the laser cut pattern imparted to the deposited film/tube and the film/tube having been electropolished.
Figure 26:
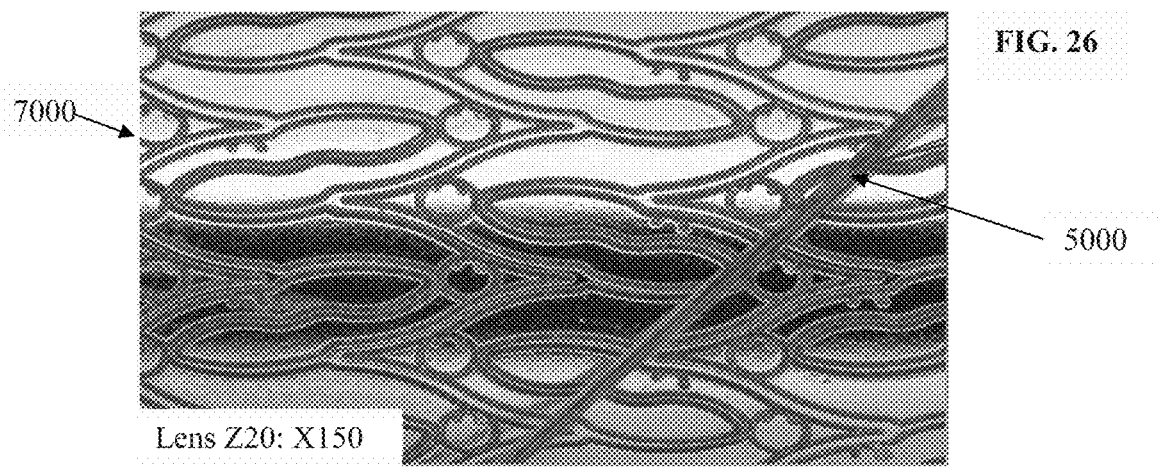
FIG. 26 shows an enlarged view of a portion of the electropolished deposited film/tube on a substrate, with a human hair as a visual reference.

One embodiment of the electropolished deposited tube on a substrate 7000 is shown in FIGS. 25 and 26. FIG. 25 shows the deposited film/tube 7200 on the substrate 7100, with the laser cut pattern 7300 imparted to the deposited film/tube 7200. The surface of the deposited film 7200 has been electropolished while on the substrate. FIG. 26 shows the electropolished deposited film/tube on a substrate 7000, with a human hair 5000 as a visual reference.

Figure 27:
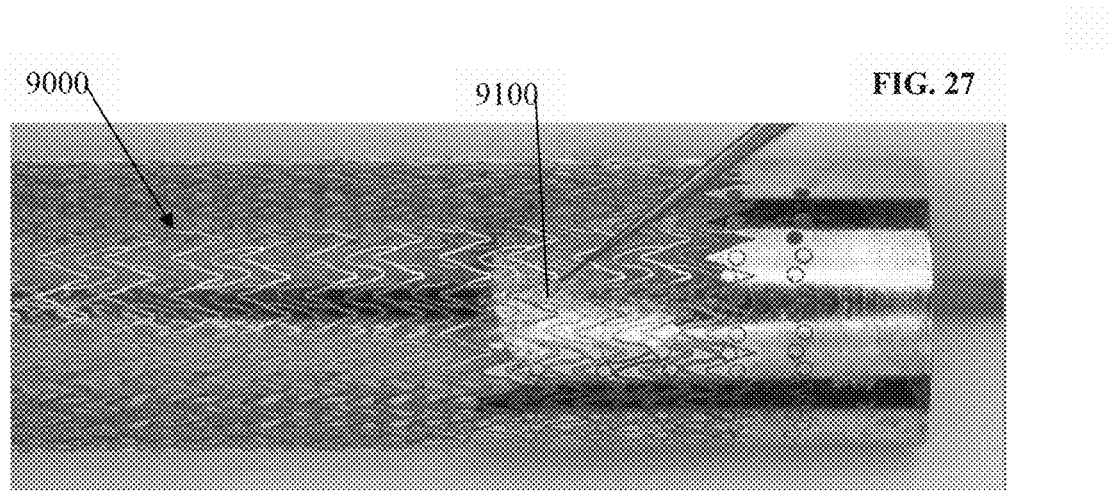
FIG. 27 shows one embodiment of the device formed by the present method, partially released from the substrate.

Finally, the device is separated from the substrate by submersion in an acid bath which selectively dissolves the substrate material away leaving the finished device. FIG. 27 shows one embodiment of the device 9000 formed by the present method, partially released from the substrate 9100.

Alternatively, the substrate may be a solidified salt or a low melting point metal, and the substrate and device may be heated to a temperature above the melting point of the substrate but below the melting or heat treatment temperatures of the device.

Figure 28:
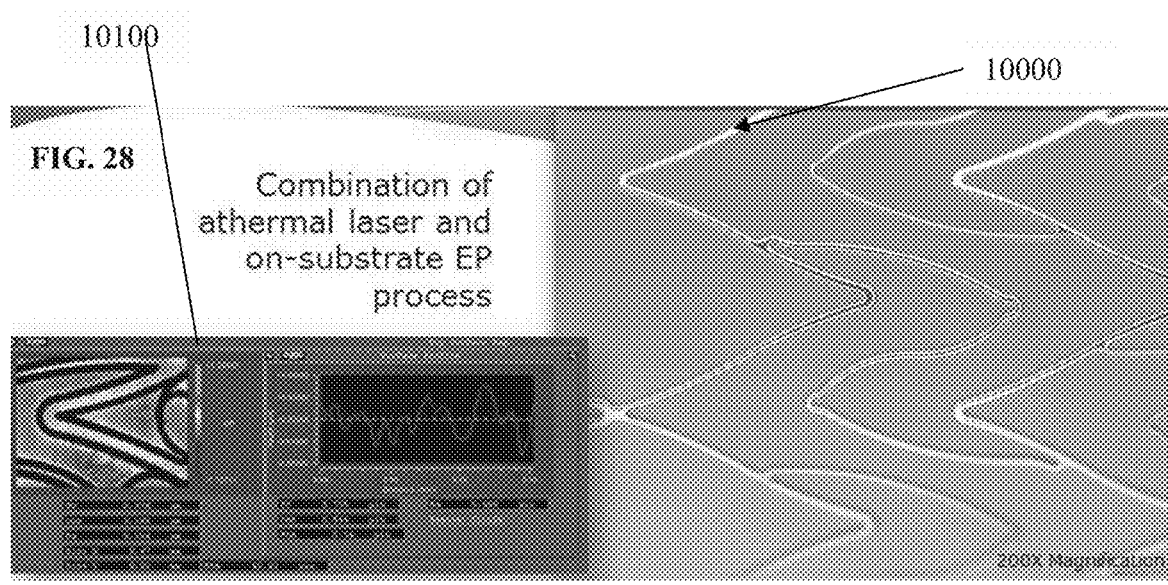
FIG. 28 shows one embodiment of the resultant device 1000 formed by an embodiment of the present method, under 200× magnification, as well as analysis of the surface profile of the formed device.
Figure 29:
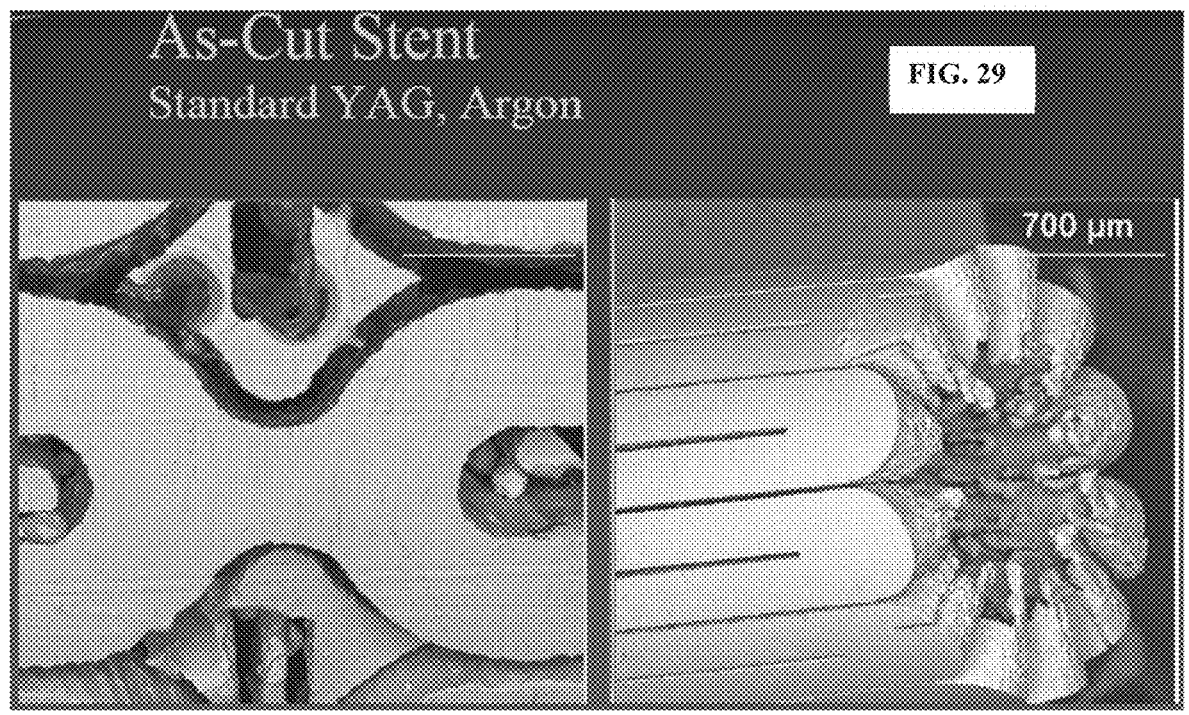
Figure 30:
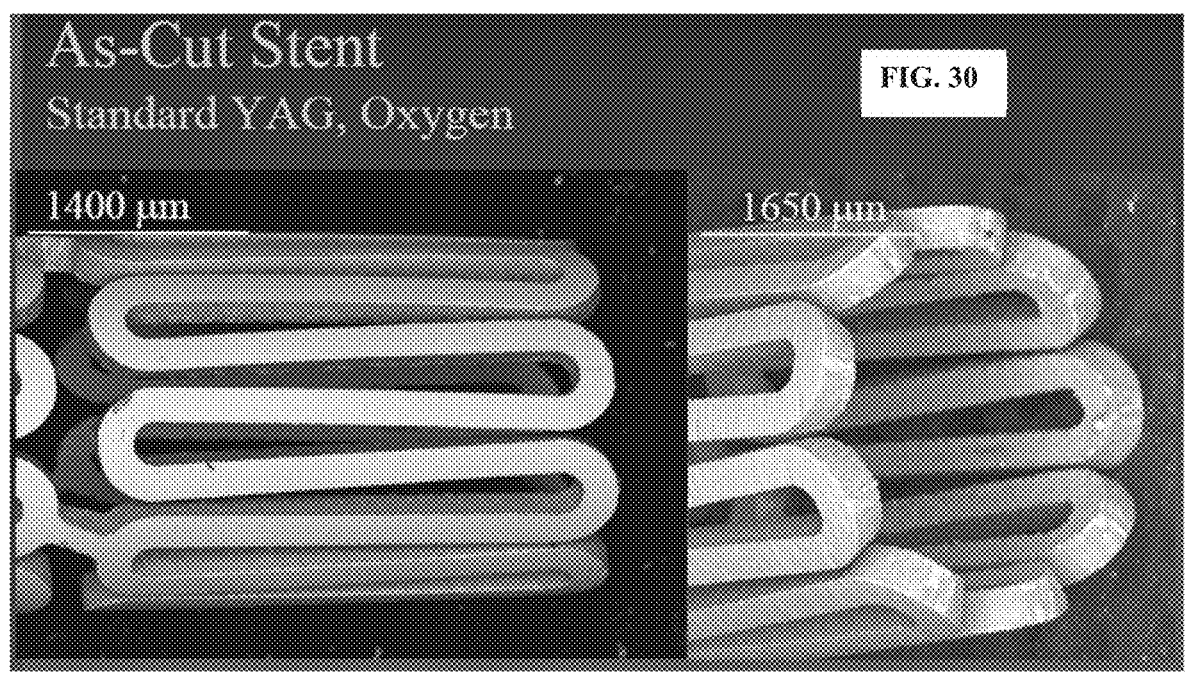
Figure 33:
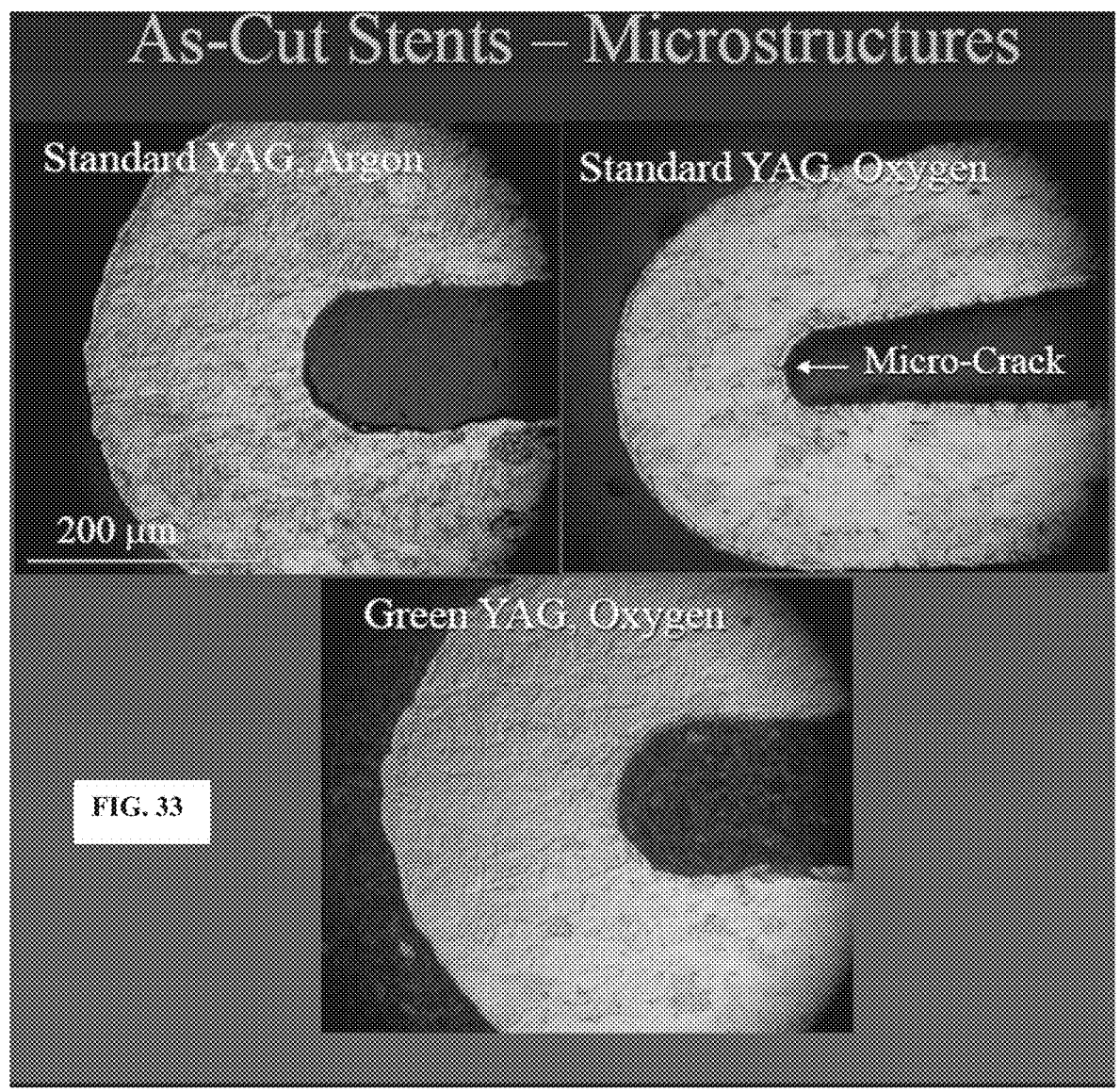

FIG. 28 shows one embodiment of the resultant device 10000 formed by an embodiment of the present method, under 200× magnification, as well as analysis 10100 of the surface profile of the formed device 10000, demonstrating the uniformity achieved with the present method combining athermal laser ablation and on-substrate electropolishing processes.

FIGS. 29-33 show SEM images of as-cut stents using standard YAG lasers with Argon cover gas, using standard YAG lasers with Oxygen assist gas, and using green YAG lasers with Oxygen assist gas. As can be seen when compared to FIG. 24, which shows SEM images of the as-cut devices formed by the present method, the present method results in cleaner cuts and improved as-cut device edge quality In some embodiments, the devices formed by the present methods may further include grooved features on at least one surface of the device. In other embodiments, the device may include a plurality of microgrooves imparted onto the luminal and/or abluminal surface of the device, as is more fully described in U.S. patent application Ser. No. 13/654,923, filed Oct. 18, 2012, which is commonly assigned with the present application and is hereby incorporated by reference in its entirety. The plurality of microgrooves may be formed either as a post-deposition process step, such as by etching, or during deposition, such as by depositing the stent-forming material onto a mandrel which has a microtopography on the surface thereof which causes the metal to deposit with the microgroove pattern as part of the deposited material.

The monolithic devices may be formed of metals, pseudo-metals, polymers, composites, ceramics, and/or the like or combinations thereof. In some embodiments, materials to make the medical devices are chosen for their biocompatibility, mechanical properties, i.e., tensile strength, yield strength, and their ease of deposition include the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, nitinol alloys, and stainless steel.

In some embodiments, the monolithic devices may be fabricated by a procedure, as described in U.S. application Ser. No. 13/788,081, filed Mar. 7, 2013 or in U.S. patent application Ser. No. 13/099,980, filed May 3, 2011, herein incorporated by reference in their entireties. In one embodiment, a coating of deposited metal film or polymer is about 0.1-100.0 microns in a tube form, which is laser cut using ultra short pulsed femtosecond laser to minimize heat affected zones and recast. The final monolithic device may be heat treated to optimize spring back effects. The stent's one piece construction allows many advantages over many currently available braided stent designs, such as a lower profile, self-expanding, and ease of manufacturing. Alternatively, the monolithic devices may be produced from drawn metal or polymer tubing, wrought tubing, provided that fatigue life is adequate. Radiopaque markers could be added as an interspersed deposited layer if vacuum deposition is used. Different metal layers may be used to form the monolithic devices.

In some embodiments, the method further comprises the step of patterning at least one surface of the monolithic device. In some embodiments, the patterning comprises laser patterning to impart at least one feature on the at least one surface of the monolithic device. In some embodiments, the pattern is a series of grooves on at least one surface of the monolithic device, preferably the surface that will comprise the inner diameter of the finished stent. In other embodiments, the pattern may be a plurality of microgrooves imparted onto the luminal and/or abluminal surface of the monolithic device, as is more fully described in U.S. patent application Ser. No. 13/654,923, filed Oct. 18, 2012, which is commonly assigned with the present application and is hereby incorporated by reference in its entirety. The plurality of microgrooves may be formed either as a post-deposition process step, such as by etching, or during deposition, such as by depositing the stent-forming material onto a mandrel which has a microtopography on the surface thereof which causes the metal to deposit with the microgroove pattern as part of the deposited material.

The monolithic devices may be intravascular stents, stent-grafts, grafts, heart valves, venous valves, filters, occlusion devices, catheters, sheaths, osteal implants, implantable contraceptives, implantable antitumor pellets or rods, shunts and patches, pacemakers, needles, temporary fixation rods, medical wires or medical tubes for any type of medical device, or other implantable medical devices, as will also be hereinafter described. A pacemaker (or artificial pacemaker, so as not to be confused with the heart's natural pacemaker) is a medical device that uses electrical impulses, delivered by electrodes contacting the heart muscles, to regulate the beating of the heart. The electrodes may be covered by tubing or other material that includes a surface that may require endothelialization and grooves thereon. Earrings and other piercings may benefit from the topographical features, as well as any other implant, whether the implant is an organic, inorganic, mechanical, electrical, or biological device.

The monolithic device may be used with any type of cell, which cell has a cellular membrane. Most distinct cell types arise from a single totipotent cell that differentiates into hundreds of different cell types during the course of development. Multicellular organisms are composed of cells that fall into two fundamental types: germ cells and somatic cells. During development, somatic cells will become more specialized and form the three primary germ layers: ectoderm, mesoderm, and endoderm. After formation of the three germ layers, cells will continue to specialize until they reach a terminally differentiated state that is much more resistant to changes in cell type than its progenitors. The ectoderm differentiates to form the nervous system (spine, peripheral nerves and brain), tooth enamel and the epidermis (the outer part of integument). It also forms the lining of mouth, anus, nostrils, sweat glands, hair and nails. The endoderm forms the gastrointestinal tract cells, the respiratory tract cells, the endocrine glands and organ cells, the auditory system cells, and the urinary system cells. The mesoderm forms mesenchyme (connective tissue), mesothelium, non-epithelial blood cells and coelomocytes. Mesothelium lines coeloms; forms the muscles, septa (cross-wise partitions) and mesenteries (length-wise partitions); and forms part of the gonads (the rest being the gametes).

The methods may also apply to many other uses. In general stenting, the methods may be applied when permit tighter radial pressure control, fine features, high conformability, coverage control, lower profile, radiopacity, and/or the like are important. The methods may be applied to integral baskets or filters, e.g., embolic protection, retrieval baskets (e.g., kidney stones), dialysis filters, and/or the like. The methods may be applied to clot retrieval, where a wedge cross section (smaller at outer diameter than inner diameter) may aid penetration and anchoring. The methods may be applied to patches, e.g., perforation, wound closure, spinal disc containment, and/or the like. The methods may be applied to plaque containment (e.g., carotid, coronary, and/ or the like). The methods may be applied to flow diversion or flow obstruction. The methods may be applied to SFA, with high axial conformability via weak/strong segments. The methods may be applied to small vessels, i.e. ED, BTK, distal coronary, and/or the like. The methods may be applied to scaffolding for tissue growth, i.e. heart valves, PFO (septal defects closure), and/or the like. The methods may be applied to drainage shunts, such as urethral, bile, ocular, ear, wound, and/or the like. The methods may be applied to grafts, such as SVG, AAA, renal, and/or the like. The methods may be applied to drug delivery (maximize surface area and coverage), or drug eluting balloon cages. The methods may be applied to local cancer treatment. The methods may be applied to coronary sinus support. The methods may be applied to tissue scaffolds. The methods may be applied to bifurcations (compliant mesh section allowing additional stent to pass through to side branch). The methods may be applied to cranial meshes with or without anchoring. The methods may be applied to urinary tract stents, whether permanent or temporary, or in some instances made of resorbable materials. The methods may be applied to contraceptive devices, such as a filter in the fallopian tube (permanent, resorbable, or removable), and/or the like. The methods may be applied to hernia meshes, such as laparoscopy-compatible. The methods may be applied to glaucoma shunts. The methods may be applied to neural stimulation anchor elements. The methods may be applied to bronchial "stents." The methods may be applied to esophageal stents, including with drug elution. The methods may be applied to Eustachian tube shunts. The methods may be applied to nasal support for rhinoplasty. The methods may be applied to delivery system linings. The methods may be applied to anchors, such as for tissue attachment, neuro stimulation, pacing leads, vessel attachment (CABG), and/or the like. The methods may be applied to cochlear implants. The methods may be applied to pediatric devices, which need smaller sizes or growth accommodation, e.g., stiff axial ribs for vessel incorporation with weak bridges that allow for vessel diametric growth (may need coatings, etc. to prevent incorporation until maturity). The methods may be applied to sensor elements, such as for coronary mapping, force feedback, and/or the like. The methods may be applied to steerable catheters. The methods may be applied to ablation tips. The methods may be applied to RO position markers, whether retrievable or permanent. The methods may be applied to MEMS devices, such as actuators, springs, valves, and/or the like. The methods may be applied to micro-robotics components.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

The invention claimed is:

1. A monolithic medical apparatus comprising:
    a. a plurality of main body members wherein each main body member comprises a ring member, wherein the ring member comprises a plurality of struts configured in an undulating pattern of peaks and troughs;
    b. a plurality of first bridge members and a plurality of second bridge members, the plurality of first bridge members and the plurality of second bridge members having a substantially curvilinear body, wherein the plurality of first bridge members and/or the plurality of second bridge members interconnect a main body member of the plurality of main body members to an adjacent main body member of the plurality of main body members, and the first bridge members have a stiffness less than the second bridge members; and
    c. wherein at least one bridge member of the plurality of first bridge members and at least one bridge member of the plurality of second bridge members connect an intermediate position substantially halfway between a peak and a trough of a first strut on a main body member to an intermediate position substantially halfway between a peak and a trough of an adjacent second main body member.

2. The apparatus of claim 1, wherein adjacent main body members are interconnected by bridge members intermediate every peak or trough of the main body members.

3. The apparatus of claim 1, wherein at least one strut has a distorted configuration, as to allow clearance for at least one bridge member of the plurality of first bridge members or the plurality of second bridge members when the apparatus is crimped, and wherein the apparatus is retrievable.

4. The apparatus of claim 1, wherein at least one second bridge member of the plurality of second bridge members further comprises a nipple at a hinge point of said at least one second bridge member; wherein at least one connection point between a main body member and a bridge member is keyholed; wherein the bridge members are configured to nest when the apparatus is crimped; wherein the first bridge members and second bridge members have a bridge stiffness ratio between about 1:4 and about 1:6.5; wherein the first bridge members have a width less than that of the second bridge members.

5. The apparatus of claim 1, further comprising at least one end body member connected to a first main body member; wherein a first end body member further comprises at least one anchoring member; wherein a second end body member further comprises at least one flaring member; wherein at least a portion of the apparatus comprises a high density pattern for patch applications.

6. The apparatus of claim 1, wherein a geometry of a plurality of bridge members is configured to control stiffness of each of the plurality of bridge members in different directions; wherein the bridge members are relatively weak in the radial direction and relatively stiff in the length axis; wherein a pattern of bridge members is configured to interlock during stretching to limit expansion in the outside of a bend; wherein at least a plurality of bridge members are configured to contact each other when the apparatus is in a vessel loaded position; wherein a pattern of bridge members is configured to fold inward when the apparatus compressed to a crimped state; wherein a pattern of bridge members varies in population along a length of the apparatus.

7. The apparatus of claim 1, wherein the apparatus is comprised of any one of the following: metals, pseudometals, polymers, composites, ceramics, and/or combinations thereof.

8. The apparatus of claim 1, wherein the apparatus is comprised of any one of the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, nitinol alloys, and stainless steel.

9. The apparatus of claim 1, wherein the plurality of main body members, the first plurality of bridge members, or the second plurality of bridge members further comprise a wedge or trapezoidal shaped cross section.

10. The apparatus of claim 1, wherein spacing between bridge members in an operating state is between about 0.1-100.0 microns.

11. The apparatus of claim 1, wherein the plurality of main body members, the first plurality of bridge members, or the second plurality of bridge members have a thickness between about 0.1-100.0 microns.

12. The apparatus of claim 1, wherein the plurality of main body members have a width of about 12 microns and the first plurality of bridge members and the second plurality of bridge members have a width of about 18 microns or about 24 microns.

13. The apparatus of claim 1, having a collapsed state with a diameter about 0.2 mm and about 2.0 mm and a expanded state between about 2 mm and about 7 mm.

14. The apparatus of claim 1, wherein the plurality of main body members, the first plurality of bridge members, or the second plurality of bridge members further comprise a radiopaque layer of Tantalum.

15. The apparatus of claim 1, wherein the plurality of main body members further comprises tapering between a connection point with the first plurality of bridge members, or the second plurality of bridge members and a peak or trough point of the plurality of main body members.

16. The apparatus of claim 1, wherein at least one strut of the plurality of struts is tapered toward its midpoint.

17. The apparatus of claim 1, wherein at least some of the plurality of first bridge members have non-uniform body widths along a longitudinal axis thereof.

18. The apparatus of claim 1, wherein at least some of the plurality of second bridge members have non-uniform body widths along a longitudinal axis thereof.

19. A monolithic medical apparatus comprising:
a. a plurality of main body members wherein each main body member comprises a ring member, wherein the ring member comprises a plurality of struts configured in an undulating pattern of peaks and troughs;
b. a plurality of first bridge members and a plurality of second bridge members, the plurality of first bridge members having a stiffness less than the plurality second bridge members and the plurality second bridge members having a second bridge member width larger than a first bridge member width;
c. wherein the plurality of first bridge members and/or the plurality of second bridge members interconnect a main body member of the plurality of main body members to an adjacent main body member of the plurality of main body members, and the first bridge members have a stiffness less than the second bridge members; and
d. further wherein at least one bridge member of the plurality of first bridge members and at least one bridge member of the plurality of second bridge members connect an intermediate position substantially halfway between a peak and a trough of a first strut on a main body member to an intermediate position substantially halfway between a peak and a trough of an adjacent second main body member.

20. The apparatus of claim 19, the plurality of first bridge members and plurality of second bridge members having a curvilinear "s"-shaped or "z"-shaped body having peaks and troughs aligned with the main body peaks and troughs.

* * * * *